(12) United States Patent
Mohapatra et al.

(10) Patent No.: US 6,489,306 B2
(45) Date of Patent: *Dec. 3, 2002

(54) METHOD OF INTRANASAL GENE TRANSFER FOR PROTECTION AGAINST RESPIRATORY INFECTION

(75) Inventors: Shyam S. Mohapatra; Hiroto Matsuse; Aruna K. Behera; Mukesh Kumar, all of Tampa, FL (US)

(73) Assignee: University of South Florida, Tampa, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/259,411

(22) Filed: Feb. 23, 1999

(65) Prior Publication Data

US 2001/0006951 A1 Jul. 5, 2001

Related U.S. Application Data

(60) Provisional application No. 60/075,588, filed on Feb. 23, 1998.

(51) Int. Cl.$^7$ .................. A61K 48/00; C12N 15/74; C12N 5/00; C12N 15/63
(52) U.S. Cl. .................. 514/44; 435/320.1; 435/325; 435/455; 435/69.1; 424/188.1; 536/23.5
(58) Field of Search ................... 536/23.5; 514/44; 435/69.1, 320.1, 455, 325; 424/188.1

(56) References Cited

U.S. PATENT DOCUMENTS

| | | | |
|---|---|---|---|
| 4,439,196 A | 3/1984 | Higuchi | 424/473 |
| 4,447,224 A | 5/1984 | DeCant, Jr. et al. | 604/67 |
| 4,447,233 A | 5/1984 | Mayfield | 604/152 |
| 4,475,196 A | 10/1984 | LaZor | 714/46 |
| 4,486,194 A | 12/1984 | Ferrara | 424/449 |
| 4,487,603 A | 12/1984 | Harris | 604/152 |
| 4,925,678 A | 5/1990 | Ranney | 424/493 |
| 4,959,217 A | 9/1990 | Sanders | 424/470 |
| 5,167,616 A | 12/1992 | Haak et al. | 604/20 |
| 5,169,383 A | 12/1992 | Guory et al. | 604/20 |
| 5,225,182 A | 7/1993 | Sharma | 424/93.71 |

OTHER PUBLICATIONS

Adams, R.B., Planchon S.M., Roche J.K. IFN–gamma modulation of epithelial barrier function time course, reversibility, and site of cytokine binding. J. Immunol. 1993; 150–2356–63.

Armstrong, DS and Menahem S. Cardiac arrhythmias as a manifestation of acquired heart disease in association with pediatric respiratory syncytial virus infection. J. Ped. Child Health. 1993; 29:309–311.

Arnold R, Werchau H, Konig W. Expression of adhesion molecules (ICAM–1, LFA–3) on human epithelial cells (A549) after respiratory syncytial virus infection. Int Arch Allergy And Immunol. 1995;107:392–93.

Arnold R, Konig W. ICAM–1 expression and low–molecular–weight G–protein activation of human bronchial epithelial cells (A549) infected with RSV. J Leuk Biol 1996;60:766–71.

Ausubel et al., Current Protocols in Molecular Biology, John Wiley & Sons, Baltimore, Maryland (1989).

Barik S. Transcription of human respiratory syncytial virus genome RNA in vitro: requirement of cellular factor(s). J. Virol. 1992;66:6813–6818.

Becker S et al. Interleukin–8 Expression in Normal Nasal Epithelium and its Modulation by Infection with Respiratory Syncytial Virus and Cytokines Tumor Necrosis Factor, Interleukin–1 and Interleukin–6. AM J. Respir. Cell Mol. Biol. 1993. 8:20–7.

Beretta. L.. M. Gabbay, R. Berger, S.M. Hanash, and N. Sonenberg. Expression of the protein kinase PKR is modulated by IRF–1 and is reduced is 5q–associated leukemias. Oncogene. 1996; 12:1593–1596.

Birren et al (eds) Genome Analysis: A Laboratory Manual Series, vols. 1–4 Cold Spring Harbor Laboratory Press, New York (1998).

Blood 87:3822.

Boehm U., Klamp T., Groot, M., Howard J.C. Cellular responses to interferon–gamma. Annu Rev Immunol. 1997;15:749–95.

Brandt CD, Kim HW, Arrobio JO et al. Epidemiology of respiratory syncytial virus infection in Washington, D.C. III. Composite analysis of eleven consecutive yearly epidemics. Am J Epidemiol 1990; 98:355–64.

Center for Disease Control and Prevention: Respiratory syncytial virus activity: United States. 1996–1997 season, MMWR 1996;45:1053.

Chanock, R.M., H.W. Kim, C. Brandt, and R.H. Parrott. Respiratory syncytial virus. In Viral infections of humans. A.S. Evans, editor. Plenum Publishing Corp., New York. 1976; 365–382.

Chanock RM, Parott RH. Acute respiratory disease in infancy and childhood: present understanding and prospect for prevention. Pediatrics 1981;36:21–39.

(List continued on next page.)

Primary Examiner—A. M. S. Beckerleg
(74) Attorney, Agent, or Firm—Kohn & Associates, PLLC

(57) ABSTRACT

A method of preventing a respiratory infection by administering DNA which encodes IFN is provided. Also provided is a therapy for the prevention of a respiratory infection containing DNA which encodes IFN.

5 Claims, 5 Drawing Sheets

OTHER PUBLICATIONS

Chanock RM, Parrott RH, Connors M, Collins PL, Murphy BR. Serious respiratory tract disease caused by respiratory syncytial virus: prospects for improved therapy and immunization. Pediatrics 1992;90:137–43.

Choi, AM, Jacoby DB. Influenza Virus A Infection Induces Interleukin–8 Gene Expression in Human Airway Epithelial Cells. FEBS Lett. 1992; 309:327–9.

Churchill, L., F.H. Chilton, J.H. Resau, R. Bascom, W.C. Hubbard, and D. Proud. Cyclooxygenase metabolism of endogenous arachidonic acid by cultured human tracheal epithelial cells. Am. Rev. Respir. Dis. 1989; 140:449.

Churchill, L., B. Friedman, R.P. Schleimer, and D. Proud. Production of pranuloyte–macrophage colony stimulating factor by cultured human tracheal epithelial cells. Immunology. 1992; 75:189.

Chonomaitre T, Roberts NJ Jr, Douglas RG Jr., Hall CB, Simons RL. Interferon production by human mononuclear leukocytes: differences between respiratory syncytial virus and influenza virus. Infec Immun 1981;32:300–03.

Clemmens, M.J., and B.R.G. Williams. Inhibition of cell–free protein synthesis by pppA2'p5'A2'p5'A: a novel oligonucleotide synthesized by interferon–treated L cell extracts. Cell 1978; 13:565–572.

Coccia, E.M., G. Marziali, E. Stellaci, E. Perrotti, R. Ilari, R. Orsatti, and A. Battistinni. Cells resistance to interferon–β respond to interferon–γ via the Stat1–IRF–1 pathways. Virology. 1995; 211:113:122.

Cohen, B., D. Peretz, D. Vaiman, P. Benech, and J. Chebath. Enhancer–like interferon responsive sequence of the human and murine (2'–5') oligoadenylate synthetase gene promoters. EMBO J. 1988; 7:1411–1419.

Colgan, SP, Parkos CA, Matthews JB et al. IFN gamma induces a cell surface phenotype switch on T84 intestinal epithelial cells. Am J Physiol 1994; 1267;C402–10.

Collins, PL. The molecular biology of human respiratory syncytial virus (RSV) of the genus Pneumovirus. In: The Paramyxoviruses (ed. Kingsbury, DW), Plenum Press, New York, 1991; 103–162.

Collins et al., 1996.

Connors M, Kulkarni AB, Firestone CY, Holmes KL, Morse III–HC, Sotnikov AV, Murphy BR. Pulmonary histopathology induced by respiratory syncytial virus (RSV) challenge of formalin–inactivated RSV–immunized BALB/c mice is abrogated by depletion of CD4+ T cells. J Virol 1992;66:7444–51.

Connors M, Geise NA, Kulkarni AB, Firestone CY, Morse III HC, Sotnikov AV, Murphy BR. Enhanced pulmonary histopathology induced by respiratory syncytial virus (RSV) challenge of formalin–inactivated RSV–immunized BABL/c mice is abrogated by depletion of interleukin–4 (IL–4) and IL–10, J Virol 1994;68:5321–25.

Cregg JM, Vedvick TS, Raschke WC: Recent Advances in the Expression of Foreign Genes in *Pichia pastoris*, Bio/Technology 11:905–910, 1993.

Cromwell, O., Q. Hamid, CJ Corigan. J Barkans Q Meng PD Collins and A B Kay. Expression and generation of interlukin–8, IL–6 and granulocytemacrophage colony stimulating factor by bronchial epithelial cells and enhancement of IL–1β and tumor necrosis factor–α. Immunology. 1992;77:5834.

Crowe JE Jr Vaccine Aug.–Sep. 1998;16(14–15);1423–32 Immune responses of infants to infection with respiratory viruses and live attenuated respiratory virus candidate vaccines.

Culver, 1998. Site–Directed recombination for repair of mutations in the human ADA gene. (Abstract) Antisense DNA & RNA based therapeutics, Feb., 1998, Coronado, CA.

Dao, T, Takeuchi M, Fukuda S et al. Natural human IFN alpha enhances the expression of ICAM–1, integrin alpha 2 and beta 1 by a mucosal epithelial cell line. Folia Biologica. 1995; 41:213–25.

Darnell, J.E. Jr., I. M. Kerr, and G.R. Stark. Jak–STAT pathways and transcriptional activation in response to IFNs and other extracellular signalling proteins. Science. 1994; 264:1415–1421.

Darnell Jr. JE. STATs and Gene regulation. Science. 1997; 277:1630163.

Diaz–Guerra, M., C. Rivas, and M. Esteban. Inducible expression of the 2–5A synthetase/RNase–L system results in inhibition of vaccinia virus replication. Virology. 1997; 227:220–228.

Farrar, M.A., and R.D. Schreiber. The molecular cell biology of IFN–γ and its receptor. Ann. Rev. Immunol. 1993; 11:571–611.

Fixler DE. Respiratory syncytial virus infection in children with congenital heart disease. Ped Cardiol 1996; 17:163–8.

Floyd–Smith, G., E. Slattery, and P. Lengyel. Interferon action: RNA cleavage pattern of a (2'–5') oligoadenylate–dependent endonuclease. Science. 1981; 212:1020–1032.

Fujita, T., L.F. Reis, N. Wantabe, Y. Kimura, T. Taniguchi, and J. Vicek. Induction of the transcription factor IRF–1 and interferon–β mRNAs by cytokines and activators of second messenger pathways. Proc. Natl. Acad. Sci. USA. 1989; 89:9936–9940.

Garofalo R. Mei F. Espejo R. Ye G. Haeberle H. Baron S. Orga PL. Reyes VE. Respiratory syncytial virus infection of human respiratory epithelial cells up=regulates class I MHC expression through the induction of IFN–beta nd IL–1 alpha. J Immunol. 1996; 157(6):2506–13.

Gilboa, E, Eglitis, MA, Kantoff, PW, Anderson, WF: Transfer and expression of cloned genes using retroviral vectors. BioTechniques 4(6):504–512, 1986.

Graham BS, Henderson GS, Tang YW, Lu X, Neuzil KM, Colley DG. Priming Immunization determines T helper cytokine mRNA expression patterns in lungs of mice challenged with respiratory syncytial virus. J Immunol 1993;151:2032–40.

Hall CB, Walsh EE, Long CE, Schnabel KC. Immunity to and frequency of reinfection with respiratory syncytial virus. J Infect Dis 1991;163:693–98.

Hall CB, McBride JT. Respiratory syncytial virus—from chimps with colds to conundrums and cures. New Engl J Med 1991;325;57–8.

Hall CB. Prospects for a respiratory syncytial virus vaccine. Science 1994;265:1393–94.

Hall et al. 1984.

Harada H. Matsumoto M. Sato M. et al. Regulation of IFN–alpha/beta genes: evidence for a dual function of the transcription factor complex ISGF3 int he production and action of IFN–alpha/beta. Genes to Cells. 1996. 1(11):995–1005.

Holtzman MJ, B. Fredman, A. Bohrer, and J. Turk. Synthesis of the 1-0-hexadecyl molecular species of platelet–activating factor by airway epithelial and vascular endothelial cells. Biochem. Biophys. Res. Commun. 1991. 177:357.

Holtzman MJ, Brody SL, Look DC. Does gene therapy call for STAT immunity and inflammation at the epithelial barrier. Am J Respir Cell Mol Biol. 1995. 12:127–129.

Hovanessian, A.G., R.E. Brown, and I.M. Kerr. Synthesis of low molecular weight inhibitor or protein synthesis with enzyme from interferon–treated cells. Nature. 1977; 268:537–539.

Ihle, J.N. 1996. STATs: signal transducers and activators of transcription. Cell. 1996; 84:331–334.

Improta, et al. 1997.

Jin FY. Natan C. Radzioch D. Ding A. Secretory leukocyte protease inhibitor: a macrophage product induced by and antagonistic to bacterial lipopolysaccharide. Cell. 1997. 88(3):417–26.

Karupiah, G., Q. W. Xie, R. M. Buller, C. Nathan, C. Duarte, J.D. MacMicking. Inhibition of viral replication by interferon gamma induced nitric oxide synthase. Science. 1993; 261:1445–1448.

Kerr, I.M., and R.E. Brown. PppA2'p5'A2'p5'A: an inhibitor of protein synthesis synthesized with an enzyme fraction from interferon–treated cells. Proc. Natl. Acad. Sci. USA. 1978; 75:256–260.

Korutia L. Kumar R. Mechanism of interferon action: in vivo activation of 91 kDa transcription factor. Anticancer Research. 1996. 16(5A):2789–95.

Kim HW, Arrobio JO, Brandt CD et al. Epidemiology of respiratory syncytial virus infection in Washington, D.C. I. Importance of the virus in different respiratory tract disease syndromes and temporal distribution of infection. Am J Epidemiol 1973;98:216–25.

Kirshnan K. Pine R., Krolewski JJ. Kinase–deficient forms of Jak1 and Tyk2 inhibit interferon alpha signalling in a dominant manner. Eur J Biochem 1997. 247(1):298–305.

Kwon, OJ, BT Au, PD Collins, JN Baraniuk, IM Adcock, KF Chung, and PJ Barnes. Inhabitation of interlukin–8 expression by dexamethasone in human cultured airway epithelial cells. Immunology. 1994. 81:389.

Lemen, 1995.

Li XM, Chopra RK, Chou TY, Schofield BH, Wills–Karp M, Huang SK J Immunol Oct. 15, 1996;157(8):3216–9 Mucosal IFN–gamma gene transfer inhibits pulmonary allergic responses in mice.

Li XM, Chopra RK, Chou TY, Schofield BH, Wills–Karp M, Huang SK. Mucosal IFN–? gene transfer inhibits pulmonary allergic responses in mice. J Immunol 1996;157:3216–19.

Marini, et al. 1992.

Matsuzaki Z, Okamoto Y, Sarashina N, Ito E, Togawa K, Saito I. Induction of Intercellular adhesion molecule–1 in human nasal epithelial cells during respiratory syncytial virus infection. Immunology 1996;88:565–68.

Merolla, et al. 1995.

McIntosh K, Chanock RM. Respiratory syncytial virus. In: Fields BN, Knipe DM. (Eds.), Virology, 2nd ed. Raven Press, New York, 1990, pp. 1045–1072.

Mok JYK, Simpson H. Symptoms, atopy and bronchial reactivity after lower respiratory infection in children. Arch Dis Child 1984;59:299–305.

Mosmann TR, Coffman RI. Th1 and Th2 cells: different patterns of lymphokine secretion lead to different functional properties. Annu Rev Immunol 1989;7:145–73.

Muller U, Steinhoff U, Reis LFL, Hemmi S, Pavlovic J, Zinkemagel RM, Aguet M. Functional role of type I and type II interferons in antiviral defense. Science 1994;264:1918–21.

Murray AR, Dowell SF. Respiratory syncytial virus: not just for kids. Hospital Practice 1997;15:87–104.

Murray et al., 1997.

Naik, et al. 1997.

Nilsen, T.W., P.A. Maroney, and C. Baglioni. Synthesis of (2',5') oligoadenylate and activation of an endoribonuclease in interferon–treated HeLa cells infected with reovirus. J. Virol. 1982; 42:1039–1045.

Noah, TL, Becker S. Respiratory Syncytial Virus–induced Cytokine Production by a Human Bronchial Epithelial Cell Line. Am. J. Physiol. 1993; 265:L472–8.

Openshaw PJM. Flow cytometric analysis of pulmonary lymphocytes from mice infected with respiratory syncytial virus. Clin Exp Immunol 1989;75:324–28.

*PCR Protocols: A Guide To Methods And Applications,* Academic Press, San Diego, CA (1990).

Pene J, Rousset F, Briere F, Chretien I, Bonnefoy JY, Spits H, Yokota T, Arai N, Arai KI, Banchereay J, Vries J de. IgE production by human lymphocytes is induced by interleukin–4 and suppressed by interferons gamma, alpha, and prostaglandin E2. Proc Natl Acad Sci U.S.A 1988;85:6880–84.

Perbal, *A Practical Guide to Molecular Cloning,* John Wiley & Sons, New York (1988), and in Watson et al., *Recombinant DNA,* Scientific American Books, New York.

Persson, CGA, Erjefalt JS Anderson M et al. Epithelium, microcirculation, and eosinophils—new aspects of the allergic airway in vivo. Allergy. 1997. 52:241–255.

Pine, R. Constitutive expression of an ISGF2/IRF1 transgene leads to interferon independent activation of interferon–inducible genes and resistance to virus infection. J. Virol. 1992; 66:4470–4478.

Pottratz T. Weir Al. Gamma–interferon inhibits *pneumocystis carinii* attachment to lung cells by decreasing expression of lung cell–surface integrins. Eur J Clin Invest. 1997 27(1):17–22.

Pullen et al. 1982.

Robinson et al. 1997.

Roman M, Calhoun WJ, Hinton KL, Avendano LF, Simon V, Escobar AM, Gaggero A, Diaz PV. Respiratory syncytial virus infection in infants is associated with predominant Th–2–like response. Am J Resp Crit Care Med 1997;156:190–95.

Sabauste, MC et al. Infection of human respiratory epithelial cell line with rhinovirus. Induction of cytokine release and modulation of susceptibility to infection by cytokine exposure. J. Clin Invest, 1995 96:549.

Sambrook et al., *Molecular Cloning: A Laboratory Manual,* Cold Spring Harbor Laboratory Press, New York (1989).

Schindler, C., J.E. Darnell Jr. Transcriptional responses to polypeptide ligands: the JAK–STAT pathways. Annu, Rev. Biochem. 1995; 64:621–651.

Schwarze J, Hamelmann E, Bradley KL, Takeda K, Gelfand EW. Respiratory syncytial virus infection results in airway hyperresponsiveness and enhanced airway sensitization to allergen. J Clin Invest 1997;100:226–233.

Sethi SK, Bianco A, Allen JT, Knight RA, Spiteri MA. Interferon–gamma down–regulates the rhinovirus–induced expression of intercellular adhesion molecule–1 (ICAM–1) on human airway epithelial cells. Clin Ecp. Immunol 1997;110:362–369.

Sethi SK, Bianco A, Allen JT, Knight RA, Spiteri MA Clin Exp Immunol 1997 Dec;110(3):362–9 Interferon–gamma (IFN–gamma) down–regulates the rhinovirus–induced expression of intercellular adhesion molecule–1 (ICAM–1) on human airway epithelial cells.

Shelhamer JH et al. NIH Conference. Airway Inflammation. Ann Int Med. 1995. 123:288–304.

Silverman, R.H. 2–5A dependent RNase L: a regulated endoribonuclease in the interferon system. In G. D'Alessio, 2nd, and J. F. Riordan (ed.), Ribunuclease: structure and function. Academic Press, New York, N. Y. 1997: 515–551.

Sly PD, Hibbert ME. Childhood asthma following hospitalization with acute viral bronchiolitis in infancy. Pediatr Pulmonol. 1989;7:153–58.

Sousa, et al. 1994.

Stark, G.R., W.J. Dower, R.T. Schimke, R.E. Brown, and I.M. Kerr. 2–5A synthetase: assay, distribution and variation with growth or hormone status. Nature. 1979; 278:471–473.

Stark JM, Godding V, Sedgwick JB, Busse WW. Respiratory syncytial virus infection enhances neutrophil and eosinophil adhesion to cultured respiratory epithelial cells. Roles of CD18 and intercellular adhesion molecule–1. J Immunol 1996;156:4774–82.

Tautz D, Renz M. An optimized freeze–squeeze method for the recovery of DNA fragments from agarose gels. Anal Biochem 1983;132:14–19.

Taylor G, Stott EJ, Hayle AJ. Cytotoxic lymphocytes from the lung of mice infected with respiratory syncytial virus. J Gen Virol 1985;66:2533–38.

Testoni et al, 1996.

Valente, G., L. Ozmen, F. Novelli, M. Guena, G. Palestro, G. Forni, and G. Garotta. Distribution of IFN–γ receptor in human tissues. Eur. J. Immunol. 1992; 22:2403–2412.

Walsh JA. Establishing Health Priorities in the Developing World. United Nations Development Programme, New York, 1988.

Warren KS. New scientific opportunities and old obstacles in vaccine development. Proc Natl Acad Sci USA 1986;83:9275–7.

Weiss ST, Tager IB, Munoz A, Speizer FE. The relationship of respiratory infection in early childhood to the occurrence of increased levels of bronchial responsiveness and atopy. Am Rev Res Dis 1985;131:573–78.

Will A, Hemmann U, Horn F, Rollinghoff M, Gessner A. Intracellular murine IFN–? mediates virus resistance, expression of oligodenylate synthetase, and activation of STAT transcription factor. J Immunol 1996;4576–83.

Williams, B.R.G., R.R. Golgher, R.E. Brown. C.S. Gilbert and I.M. Kerr. Natural occurrence of 2–5A in interferon–treated EMC virus–infected L cells. Nature. 1979;282:582–586.

Wreschner, D.H., J.W. McCauley, J.J. Skehel, and I.M. Kerr. Interferon action: sequence specificity of the ppp(A2'p)nA–dependent ribonuclease. Nature. 1981;289:414–417.

Wyde PR Antiviral Res Aug. 1998;39(2):63–79 Respiratory syncytial virus (RSV) disease and prospects for its control.

McCluskie et al., "Route and Method of Delivery of DNA Vaccine Influence Immune Responses in Mice and Non–human Primates.", Molecular Medicine, vol. 5 : 287–300, May 1999.*

Crowe JE Jr., "Immune responses of infants to infection with respiratory viruses and five attenuated respiratory virus candidate vaccines.", Vaccine, vol. 16: 1423–1432, Sep. 1998.*

Tang et al., "Determinants and kinetics of cytokine expression patterns in lungs of vaccinated mice challenged with respiratory syncytial virus," Vaccine, vol. 15 (6–7): 597–602, May 1997.*

Li et al., "Mucosal IFN–gamma gene transfer inhibits pulmonary allergic responses in mice." J. Immuno. vol. 157 (8): 3216–9, Oct. 1996.*

Wyde PR., "Respiratory syncytial virus (RSV) disease and prospects for its control." Antiviral Res. vol. 39 (2): 63–79, Aug. 1998.*

Dow et al., "Systemic and local interferon.gamma. gene delivery to the lungs for treatment of allergen–induced airway hyperresponsiveness in mice," Hum gene ther. Col. 10(12): 1905–1914, Aug. 1999.*

Sethi et al., "Interferon–gamma (IFN–gamma) down–regulates the rhinovirus–induced expression of intercellular adhesion molecule–1 (ICAM–1) on human airway epithelial cells." Clin. Exp. Immunol., vol. 110 (3): 362–9, Dec. 1997.*

Robinson et al., "Predictive assessment of respiratory sensitizing potential of proteins in mice." Toxicol. Chem. Respir. Hypersensitivity: 135–150, 1997.*

Verma et al.; Gene therapy—promises, problems and prospects, 1997. Nature vol. 389: 239–242.*

Marshall; Gene Therapy's Growing Pains, 1995 Science vol. 269: 1050–1055.*

Orkin et al.; Report and Recommendations of the Panel to Assess the NIH Investment in Research on Gene Therapy, 1995.*

* cited by examiner (A)

(B)

(C)

METHOD OF INTRANASAL GENE TRANSFER FOR PROTECTION AGAINST RESPIRATORY INFECTION

CROSS REFERENCE TO RELATED APPLICATIONS

This application is based on a Provisional Application, Ser. No. 60/075,588, filed Feb. 23, 1998, now abandoned.

BACKGROUND OF THE INVENTION

1. Field of the Invention

A method of preventing, or decreasing the severity of symptoms associated with a respiratory viral infection in a mammal is provided. Also provided is a method of gene therapy capable of causing expression of IFNγ in respiratory cells for prevention of viral infection.

2. Description of Related Art

Respiratory viruses such as respiratory syncytial virus (RSV), the parainfluenza viruses (PIV), and the influe nza viruses cause severe lower respiratory tract diseases in infants and children throughout the world. It is also an important cause of disease in adults and is responsible for a significant amount of excess morbidity and mortality in the elderly. It also can be devastating in immunosuppressed populations (Murray et al., 1997; Pullen et al. 1982; Hall et al. 1984).

Experimental live attenuated vaccines for each of these viruses are being developed for intranasal administration in the first weeks or months of life, but none are currently FDA approved. A variety of RSV, PIV-3, and influenza virus vaccine strains have been developed by classical biological methods, evaluated extensively in preclinical and clinical studies, and shown to be attenuated and genetically stable. However, a major remaining obstacle to successful immunization of infants against respiratory virus associated disease may be the relatively poor immune response of very young infants to primary virus infection. (Crowe J. E. Jr Vaccine 1998 Aug.–Sep.;16(14–15):1423–32 Immune responses of infants to infection with respiratory viruses and live attenuated respiratory virus candidate vaccines.)

Moreover, even if one or more vaccines are approved, they may not be suitable for some populations vulnerable to RSV (e.g. very young infants and the immunosuppressed). Ribavirin and immunoglobulin preparations with high titers of RSV-specific neutralizing antibodies are currently approved for use to treat and prevent RSV infection. However, neither of these methods are cost-effective or simple to administer. New agents are needed to reduce the impact of RSV. (Wyde P. R. Antiviral Res 1998 Aug.;39(2):63–79 Respiratory syncytial virus (RSV) disease and prospects for its control.)

Data obtained from the National Respiratory and Enteric Virus Surveillance System demonstrates the seasonal pattern of RSV infection, with peak rates of 30–40% occurring at the beginning of each year (Murray et al., 1997; Pullen et al. 1982; Hall et al., 1984). RSV infection is commonly associated with interstitial lung diseases, such as bronchiolitis and asthma. It is a major risk factor for a number of other disease conditions, such as immunodeficiency, cardiac arrhythmia, congenital heart disease, and unusual atrial tachycardia (Sly, et al., 1989; Robinson et al. 1997; Armstrong et al. 1993; Fixler, 1996; Lemen, 1995; Persson, 1997; Shelhamer et al. 1995).

Emerging evidence points to RSV as a significant pathogen in adults and the elderly (Murray et al., 1997). In the USA alone, RSV causes about 4500 deaths per year, about 95,000 hospitalizations, and an estimated four million cases of respiratory tract infections annually (McIntosh et al., 1990; Hall, et al. 1991). RSV is also a major public health concern globally with an estimated five million deaths annually due to RSV infections (Warren, 1986; Walsh, 1988).

Although the severity of the disease decreases with repeated infection, previous RSV infection renders no or limited immunity to subsequent RSV infection (Hal, 1991).

Despite the above serious implications of RSV infection, the progress in the knowledge of the viral genes and gene products (Collins, 1991; Collins et al., 1996; Barik, 1992), an effective vaccine, or treatment against RSV, is yet to be developed.

Additionally, previous attempts to develop a vaccine using formalin inactivated RSV not only failed but exacerbated the disease when subsequent RSV infection occurred (Chanock, et al. 1992; Hall, 1994). The development of an attenuated, immunogenic and genetically stable live RSV vaccine has not been successful. An effective vaccine or treatment for RSV would be highly desirable.

Additionally, human nasal, airway, and lung epithelial cells constitute a major target for respiratory infections. Viral infection alters the expression of genes encoding a number of cytokines, chemokines and inflammatory mediators (Sabauste, et al. 1995; Choi, et al. 1992; Becker et al. 1993). However, the molecular mechanism underlying RSV infection and receptors for RSV remain to be elucidated.

The molecular pathology of RSV infection-induced inflammation, which is poorly understood, has been investigated. The alteration of gene expression for various cytokines, chemokines, and inflammatory mediators was examined using RT-PCR and ELISA assays following RSV infection of HEp-2 and BEAS-2B cells. The expression of the inflammatory cytokines IL-6, IL-8, IL-10 and IL-1β increased with the time of exposure to RSV. Both cell lines constitutively expressed IL-13 MRNA.

The expression of the chemokine, RANTES, and the broncho-constrictor, endothelin-1, were also increased after viral infection in both cell lines. The expression of other inflammatory mediators, such as inducible nitric oxide synthase (iNOS) and mucin-1 (MUC1) encoding episialin, a mucin like polypeptide, also increased after viral infection. Only the BEAS-2B cell line expressed TNF-α following viral infection. These results demonstrate that RSV infection triggers the production in these epithelial cells of several of the pro-inflammatory cytokines and mediators, responsible for the airway inflammation in both allergic and non-allergic individuals.

The secretion of cytokines by airway epithelial cells can either initiate local inflammatory responses or amplify an inflammatory event that was previously initiated by activated macrophages, eosinophils, mast cells or lymphocytes (Shelhamer et al., 1995; Holtzman, et al. 1991; Churchill, et al. 1989; Marini, et al. 1992; Churchill, et al. 1992; Kwon, et al. 1994; Sousa, et al. 1994; Cromwell, et al. 1992; Jin, et al. 1997). The epithelial cell-mediated inflammation by involve a number of cytokines and chemokines including IL-1β, IL-6, IL-8, IL-11, IFN-γ, TNF-α, GM-CSF, GRO-α, PLA-2, C3, inducible nitric oxide synthase (iNOS), MCP-1, endothelin-1 (ET-1), mucin, elastase-specific inhibitors, and secretory leukocyte proteinase inhibitor.

Available evidence suggests that the primary target of respiratory viruses are epithelial cells. Once infected, epithelial cells respond to the virus by increasing the production of a number of cytokines, which contribute to airway inflammation (Sabauste, et al. 1995; Choi, et al. 1992; Becker et al. 1993; Merolla, et al. 1995; Noah, et al. 1993; Garofalo et al. 1996). The rhinovirus infection of a transformed HBE cell line, BEAS-2B, caused the release of the granulocyte macrophage colony stimulating factor (GM-CSF), IL-6, and IL-8 (Sabauste et al. 1995). The influenza virus infection of primary cultures of human bronchial epithelial (HBE) cells induced the expression of IL-8 (Choi, et al. 1992). Also, in response to RSV infection, nasal epithelial cells and BEAS-2B cells generated IL-8 (Becker et al., 1993; Merolla et al., 1995; Noah, et al., 1993; Garofalo et al. 1996). Although the cytokine-mediated inflammatory basis of respiratory infections has been investigated, the molecular mechanisms underlying such infections remain poorly understood.

Studies in children suggest that RSV infection induce a T helper type 2-like response (Roman, et al. 1997). Also, formalin inactivated RSV induces a Th2-like response and IgE antibody production in mice (Connors, et al. 1992; Connors, et al. 1994; Graham, et al. 1993). Th2-like cells are mediated via cytokines such as IL-4, IL-5, IL-10, and IL-13 (Mosmann, et al. 1989) which are either important for IgE production or are involved in the recruitment and activation of inflammatory cells. IL-4 and IFN-γ reciprocally regulate IgE production, and RSV infection can augment IgE mediated inflammation in individuals genetically predisposed to develop atopic disease (Roman, et al. 1997). RSV infection is also associated with recurrent episodes of bronchial obstruction and exacerbation of established asthma in some children with atopic genetic predisposition (Mok, et al. 1984; Weiss, et al. 1985; Sly, et al. 1989). Acute viral respiratory tract infections also enhance sensitization to inhalant allergens in mice (Schwarze, et al. 1997). Although the mechanism underlying this synergy is not fully characterized, it may be mediated via the T cell response.

A number of investigators have examined the effect of IFNγ on epithelial cells (Boehm et al. 1997). Exposure to IFN-γ to 84% epithelial cells resulted in increased surface expression of MHC class I molecules, β-2 integrins and ICAM-1 (Colgan, et al. 1994). Pretreatment of a KB human epithelial cell with IFN-γ, augmented the expression of ICAM-1 (Dao, et al., 1995). In an effort to define the role of IFNγ on T84 epithelial cells, Adams et al., 1993 showed that only the monolayers basolateral surface was IFNγ responsive, and the microvillus surface was not. The effects of IFN-γ were recepter-ligand mediated and IFN-γ induced changes in epithelia permeability. Moreover, IFN-γ treatment of the A594 lung epithelial cells, blocked the attachment of Pneumocystis carinii, to the cells via reduced expression of β$_2$-integrins (Pottratz et al. 1997). IFNγ was also shown to decrease the susceptibility of epithelial cells to infection by rhinovirus, although rhinovirus infection did not markedly alter the expression of the receptor ICAM-1. Also, IFNFβ markedly inhibited RSV replication in a dose- and time-dependent manner, and IFN-β did not induce cell membrane damage, cause cell lysis, or inhibit cellular protein synthesis (Garofalo et al. 1996).

It would therefore be useful to develop a vaccine for preventing a respiratory viral infection by the intranasal administration of an IFN-gamma gene which can be given to an infant or other immunosuppressed individual for prophylaxis against respiratory infection, for example. RSV.

SUMMARY OF THE INVENTION

According to the present invention, a method of preventing a respiratory infection by administering DNA which encodes IFN is provided. Also provided is a therapy for the prevention of a respiratory infection containing DNA which encodes IFN.

DESCRIPTION OF THE DRAWINGS

Other advantages of the present invention will be readily appreciated as the same becomes better understood by reference to the following detailed description when considered in connection with the accompanying drawings wherein:

FIGS. 5 (B+C) Expression of IFN-γ in BALF of pIFN-γ-vaccinated and control mice following RSV infection as estimated by ELISA. Values are mean±SD (n=6); * Indicates value significant at p<0.05 when compared with different controls.

DETAILED DESCRIPTION OF THE INVENTION

Figure 1:
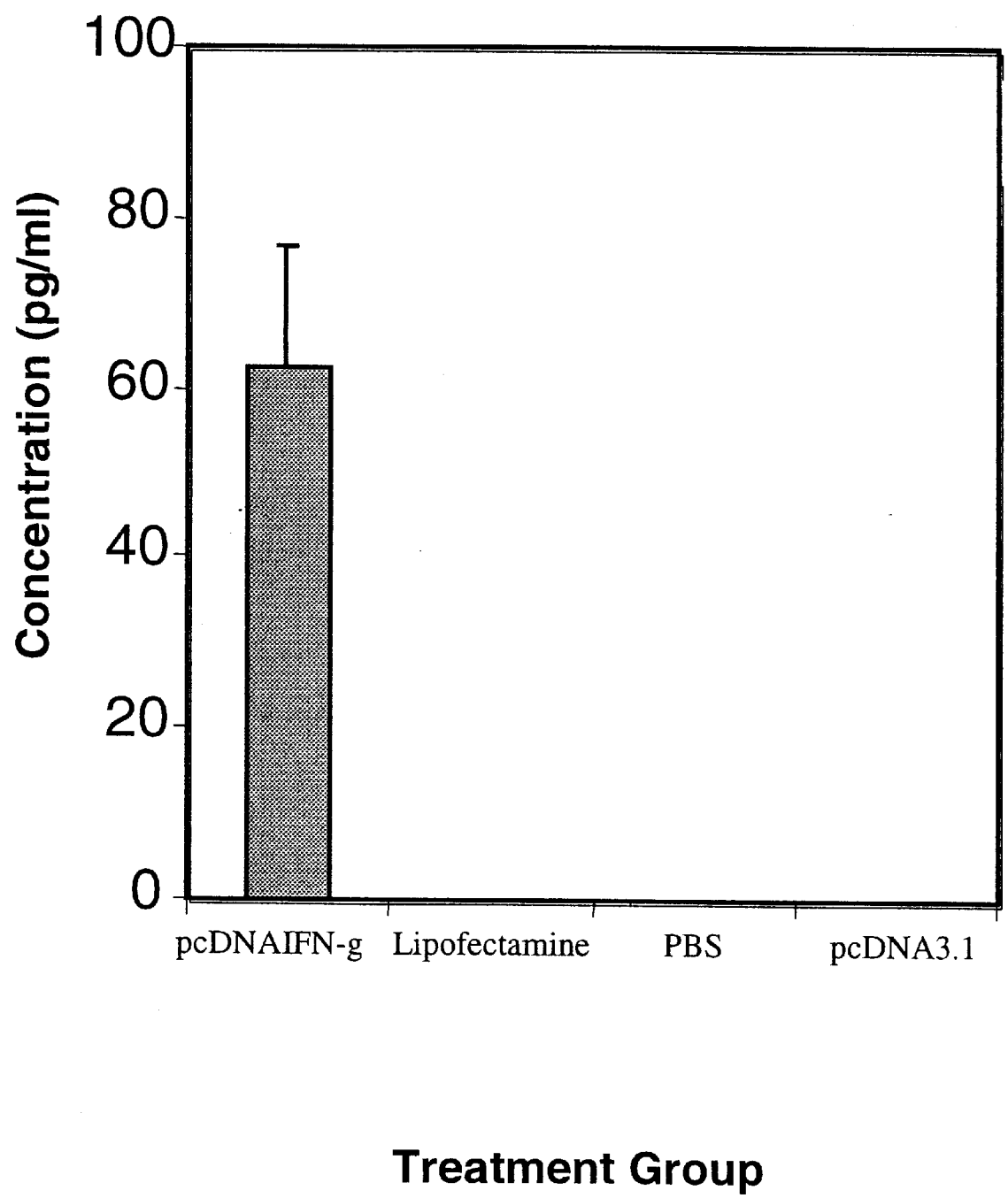
FIG. 1 shows expression of murine IFN-γ following gene transfer in BALB/c mice; Groups of mice were intranasally inoculated with either pIFN-γ (100 μg)+lipofectamine, Lipofectamine alone (50 μl), PBS (50 μl) or pcDNA3.1 (100 μg) alone, thrice with two days interval in a 50 μl volume; Seven days after the last intranasal inoculation, IFN-γ expression was detected from BALF by ELI SA, bars represent mean±SD (n=4)

Generally the present invention provides a vector and method for preventing a repiratory infection, both of which include DNA encoding the cytokine IFN-gamma which upon expression prevents infection. In a particular embodiment, the IFN-gamma vector prevents viral respiratory infection. In a preferred embodiment the IFN-gamma vector is a plasmid vector, which is non infectious, and delivers a nonintegrating DNA sequence encoding IFN-gamma for the prevention of RSV. The nature of the vector allows for transient expression of IFN-gamma. Administration of pIFN-gamma can therefore be done in anticipation of the season in which the majority of respiratory illness occurs and be protective through the season.

The applicants have found that increased levels of IFN-gamma in respiratory epithelium reduces viral replication. This was demonstrated in vitro by treating human bronchial epithelial cell cultures HEp-2 with INF-gamma, then exposing these cultures to RSV. The inventors showed a 94% reduction in RSV titers in the IFN-gamma treated cells as compared to cells not treated with IFN-gamma. In vivo demonstration was accomplished by administering pIFN-gamma to mice, then exposing them to RSV. pIFN-gamma treated animals showed an 87% reduction in RSV titers compared to control animals.

Secondly the applicants found that pIFN-gamma treatment decreased lung inflammation and pathology typically associated with RSV. In fact the cellular composition of the inflammatory response to RSV was dramatically different between animals treated or not treated with pIFN-gamma.

Thirdly, the applicants found that through pIFN-gamma administration the immune response to RSV challenge was altered from a Th2-like immune response, a pathogenic response associated with inflammation, hyperreactivity, and risk of asthma, to a Th1-like response characteristic of immune protection.

The DNA is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art.

A gene therapy according to the present invention is administered to the airways, e.g. nose, sinus, throat and lung, for example, as nose drops, by nebulization, vaporization or other methods known in the art.

In another embodiment of the present invention, the treatment includes administering to the patient an effective amount of a composition containing a recombinant construct comprising a nucleic acid sequence encoding IFN-gamma, the nucleic acid sequence being operatively linked to one or more transcription control sequences. Further, the nucleic acid sequence is expressed at or adjacent to respiratory epithelial cells and the IFN-gamma results in reduced proliferation of the respiratory infection.

Another embodiment of the present invention relates to a method of protecting a host against respiratory infection by administering to the host an effective amount of a vector containing a construct having a nucleotide sequence encoding IFN-gamma with a promoter sequence operatively attached thereto. Further, this construct contains a noninfectious, nonintegrating DNA sequence which controls the expression of the DNA sequence. Additionally, administration of the DNA is in an amount sufficient to increase levels of IFN-gamma in the respiratory tract thus providing a protective response.

IFN-γ down-regulates the Th2-like response and IgE production (Pene et al. 1988) and is a therapy for modulating pulmonary allergic responses (Li, et al. 1996).

Vectors which comprise the DNA encoding for IFN-gamma are also provided by the present invention. The vectors can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic hose systems. One of ordinary skill in the art will know which host systems are compatible with a particular vector.

IFN-γ also down-regulates the rhinovirus-induced expression of intercellular adhesion molecule-1 (ICAM-1) on human airway epithelial cells and is thereby believed to decrease the susceptibility of epithelial cells to infection (Sethi et al. 1997).

Human rhinoviruses (HRV) are a major cause of upper respiratory tract infections in man, and can exacerbate existing pulmonary disease. The major group of HRV attach to ICAM-1, which is expressed on nasal and bronchial epithelial cells. To study the influence of biological mediators on ICAM-1 expression, and consequently HRV attachment and infection, the effects of various cytokines were compared, alone and in combination, on ICAM-1 expression by an uninfected and HRV-infected bronchial epithelial cell line H292. Cytokines are known to be released soon after viral infection, such as tumour necrosis factor-alpha (TNF-alpha), IL-1beta and the chemokine IL-8 increase ICAM-1 expression on uninfected cells.

Epithelial cells infected with live HRV-14 displayed marked up-regulation of ICAM-1 compared with baseline. TNF-alpha further enhanced the HRV-induced increase in ICAM-1 expression on epithelial cells, peaking at day four after infection, while IL-8 exhibited a steady increase in ICAM-1 expression over 14 days. In contrast, IFN-gamma, a known Th1 antiviral lymphokine, while increasing the level of ICAM-1 on uninfected cells, induced a significant persistent down-regulation of ICAM-1 expression on HRV-infected epithelial cells. With combinations of TNF-alpha and IFN-gamma, ICAM-1 expression on HRV-infected cells was reduced to basal levels. The effects of IFN-gamma were paralleled by a reduction in viral titres.

The in vitro model has provided useful insights into the early pathogenic events of HRV infection at the level of the host cell-virus interaction. The data confirm that biological mediators play a crucial role in the pathogenesis as well as the course of HRV infection which is modulated by the types, and time kinetics of inflammatory cytokines in the immediate microenvironment. (Sethi S. K., Bianco A, Allen J. T., Knight R. A., Spiteri M. A. Clin Exp Immunol 1997 Dec.; 110(3):362–9 Interferon-gamma (IFN-gamma) down-regulates the rhinovirus-induced expression of intercellular adhesion molecule-1 (ICAM-1) on human airway epithelial cells).

The systemic use of IFN-γ protein to treat respiratory tract infections or allergic disease is limited because of its short half-life. Consequently, it has to be given in high or repeated doses to reach therapeutic efficacy; however, high dose IFN-γ is cytotoxic. In an effort to circumvent the drawbacks inherent with the use of IFN-γ protein, an IFN-γ gene transfer approach was used in a murine model to inhibit allergic inflammation (Li, et al. 1996). With regard to the present invention, an IFN-γ expressing plasmid vector, pIFN-γ, was used in a murine model to inhibit RSV infection. Evidence from the studies of RSV replication, BAL and histopathology of mice indicate that an IFN-γ-DNA vaccine is effective in inhibiting RSV replication and consequently infection-associated inflammation.

A major finding is the significant decrease in RSV replication detected in the pIFN-γ vaccinated mice using RT-PCR and ELISA. The transcript encoding RSV N protein was almost not detectable in majority of the pIFN-γ vaccinated mice, which suggests that overproduced IFN-γ inhibited RSV replication. There was an 87% reduction in the RSV titers in mouse vaccinated with pIFN-γ gene.

RSV infection induces inflammatory changes in the lung, which is readily detectable in BAL fluid. In normal or sham infected mice most recovered cells in BAL fluid are macrophages with less than 5% lymphocytes. RSV specific lymphocytes from the lungs of RSV infected mice by exhibit CTL activity, which peaks at days seven to nine, post infection (Taylor et al. 1985). The proportion of lymphocytes increases to about 20% between 10 and 16 days after infection and decreases thereafter (Openshaw, 1989). Consistent with these findings BAL from the lungs of pIFN-γ -administered to mice had 27% less lymphocytes compared to control groups. A small number of eosinophils were also detected in BAL of RSV infected mice, suggesting that the airway-hyper-responsiveness caused by the viral infection may be due to infiltration of these cells to the airway. RSV infection induces the expression of adhesion molecules on the bronchial epithelium, particularly ICAM-1 (Arnold et al. 1995; Matsuzaki, et al. 1996; Arnold, et al. 1996), which contributes to airway inflammation by supporting adhesion and retention of these infiltrating inflammatory cells (Stark et al. 1996).

IFN-γ levels were compared in BAL fluids following infection with RSV in control and pIFN-γ vaccinated mice. Only a three to six fold increase in IFN-γ production was found in RSV infected versus uninfected mice, which is in agreement with a low level of IFN-γ induced by RSV (Chonomaitre et al. 1981). Contrary to the expected result, the pIFN-γ administered and RSV infected compared to uninfected and IFN-gamma administered mice showed a four-fold reduction in IFN-γ levels. The reason for this reduction is unknown. It is likely that the IFN-γ is metabolized rapidly following RSV infection.

IFNs also possess important immunomodulatory functions. Because of the reciprocal regulation of T helper cell subsets, it was anticipated that the pIFN-γ vaccine would promote a Th1-like instead of a Th2-like to immune response expected against RSV. The cytokine IL-5 is an important marker of Th2-like immunity induced by RSV and it plays a pivotal role in eosinophil survival in the lung and asthma. Results from RT-PCR analysis of IL-5 mRNA expression indicated that pIFN-γ vaccination resulted in expression of IFN-γ mRNA expression and inhibited IL-5 expression in infected mice when compared to controls.

Mice lacking IFN-γ mRNA expression exhibited an upregulation in the levels of IL-5 mRNA. Furthermore, the IL-5 protein could not be detected in the BAL fluid of infected mice, which expressed significant amounts of IFN-γ and had only a few eosinophils. Together, these results suggest that pIFN-γ vaccine inhibits induction of IL-5 mRNA and may play an important role in the induction of a Th2-like immunity against RSV.

Epithelial cell damage and cellular infiltration are hallmarks of the RSV infection in humans and in various animal models. Prior administration of mice with the pIFN-γ significantly reduced epithelial cell damage and decreased interstitial and peri-bronchovascular infiltration of the cells in the lung upon RSV infection. The control RSV-infected mice predominantly showed a mononuclear cell infiltrate with very few eosinophils. No marked difference was observed between the uninfected naive and pIFN-γ administered and RSV infected mice, suggesting that pIFN-γ gene transfer does not alter the inflammatory cell population in the lung. These findings suggest that the pIFN-γ per se does not induce any inflammatory changes in the airway and the mice did not exhibit any external signs of illness, which suggests that this gene transfer method may be safe in mice. The evidence that pIFN-γ administered and RSV infected mice exhibited a normal airway phenotype suggesting that indeed the RSV replication is inhibited almost completely.

In summary, these results taken together demonstrate that a pIFN-γ gene transfer inhibits RSV replication, alters the lung cytokine pattern from a Th2- dominant to Th1-dominant milieu, and protects lung from RSV-induced epithelial damage and cellular infiltration. This transfer method renders significant protection of BALB/c mice against RSV infection. Because of the anti-viral property of IFN-γ, an IFN-γ DNA gene transfer is useful against respiratory viral infections.

The above discussion provides a factual basis for the use of a gene transfer method for the prevention of respiratory viral infection. The methods used with and the utility of the present invention can be shown by the following non-limiting examples and accompanying figures.

EXAMPLES

GENERAL METHODS

The intranasal administration of the IFN-gamma gene is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to total prevention and to improved survival rate or more rapid recovery, or improvement or elimination of symptoms and other indicators as are selected as appropriate measures by those skilled in the art.

In the method of the present invention, the IFN gene can be administered in various ways. It should be noted that the vaccine can be administered as the compound or as pharmaceutically acceptable salt and can be administered alone or as an active ingredient in combination with pharmaceutically acceptable carriers, diluents, adjuvants and vehicles. The compounds can be administered intranasally, bronchially, via inhalation pathways. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice exemplified herein which treatment has a length proportional to the length of the disease process and drug effectiveness. The doses may be single doses or multiple doses over a period of several days, but single doses are preferred.

The carrier for gene therapy can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Examples of delivery systems useful in the present invention include: U.S. Pat. Nos. 5,225,182; 5,169,383; 5,167, 616; 4,959,217; 4,925,678; 4,487,603; 4,486,194; 4,447, 233; 4,447,224; 4,439,196; and 4,475,196. Many other delivery systems and modules are well known to those skilled in the art.

A pharmacological formulation of the gene utilized in the present invention can be administered orally to the patient. Conventional methods such as administering the compounds in tablets, suspensions, solutions, emulsions, capsules, powders, syrups and the like are usable. Known techniques which deliver the vaccine orally or intravenously and retain the biological activity are preferred.

In one embodiment, the gene can be administered initially by nasal infection to increase the local levels of IFN-gamma. The patient's IFN-γ levels are then maintained by an oral dosage form, although other forms of administration, dependent upon the patient's condition and as indicated above, can be used. The quantity of vaccine to be administered will vary for the patient being treated and will vary from about 100 ng/kg of body weight to 100 mg/kg of body weight per day and preferably will be from 10 mg/kg to 10 mg/kg per day.

General Methods in Molecular Biology

Standard molecular biology techniques known in the art and not specifically described were generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al (eds) *Genome Analysis: A Laboratory Manual Series*, Vols. 1–4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al, 1996, Blood 87:3822.)

By gene therapy as used herein refers to the transfer of genetic material (e.g DNA or RNA) of interest into a host to treat or prevent a genetic or acquired disease or condition phenotype. The genetic material of interest encodes a product (e.g. a protein, polypeptide, peptide or ftunctional RNA) whose production in vivo is desired. For example, the genetic material of interest can encode a hormone, receptor, enzyme, polypeptide or peptide of therapeutic value. For a review see, in general, the text "Gene Therapy" (Advances in Pharmacology 40, Academic Press, 1997).

Two basic approaches to gene therapy have evolved: (1) ex vivo and (2) in vivo gene therapy. In ex vivo gene therapy cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the modified cells are expanded in culture and returned to the host/patient. These genetically reimplanted cells have been shown to produce the transfected gene product in situ.

In in vivo gene therapy, target cells are not removed from the subject rather the gene to be transferred is introduced into the cells of the recipient organism in situ, that is within the recipient. Alternatively, if the host gene is defective, the gene is repaired in situ [Culver, 1998]. These genetically altered cells have been shown to produce the transfected gene product in situ.

The gene expression vehicle is capable of delivery/ transfer of heterologous nucleic acid into a host cell. The expression vehicle may include elements to control targeting, expression and transcription of the nucleic acid in a cell selective manner as is known in the art. It should be noted that often the 5'UTR and/or 3'UTR of the gene may be replaced by the 5'UTR and/or 3'UTR of the expression vehicle. Therefore as used herein the expression vehicle may, as needed, not include the 5'UTR and/or 3'UTR shown in SEQ ID No: 1 and only include the specific amino acid coding region.

The expression vehicle can include a promotor for controlling transcription of the heterologous material and can be either a constitutive or inducible promotor to allow selective transcription. Enhancers that may be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene*

*Therapy*, CRC Press, Ann Arbor, Mich. (1995), Vega et al., *Gene Targeting*, CRC Press, Ann Arbor, Mich. (1995), *Vectors: A Survey of Molecular Cloning Vectors and Their Uses*, Butterworths, Boston Mass. (1988) and Gilboa et al (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of DNA viral vector for introducing and expressing recombinant sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired flnctions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on desired cell type to be targeted and will be known to those skilled in the art. For example, if breast cancer is to be treated then a vector specific for such epithelial cells would be used. Likewise, if diseases or pathological conditions of the hematopoietic system are to be treated, then a viral vector that is specific for blood cells and their precursors, preferably for the specific type of hematopoietic cell, would be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recomnbinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes and colloidal polymeric particles can also be used to introduce the non-viral vectors described above into recipient cells within the inoculated area. Such transfection vehicles are known by one skilled within the art.

Example 1

Direct DNA inoculations are administered as a method of subunit vaccination. Plasmid DNAs encoding influenza virus hemagglutinin glycoproteins have been tested for the ability to provide protection against lethal influenza challenges. In immunization trials using inoculations of purified DNA in saline, 67–95% of test mice and 25–63% of test chickens were protected against the lethal challenge. Good protection was achieved by intramuscular, intravenous and intradermal injections. In mice, 95% protection was achieved by gene gun delivery of 250–2500 times less DNA than the saline inoculations. Successful DNA vaccination by multiple routes of inoculation and the high efficiency of gene-gun delivery highlight the potential of this promising new approach to immunization.

Plasmid DNAs expressing influenza virus hemagglutinin glycoproteins have been tested for their ability to raise protective immunity against lethal influenza challenges of the same subtype. In trials using two inoculations of from 50 to 300 micrograms of purified DNA in saline, 67–95% of test mice and 25–63% of test chickens have been protected against a lethal influenza challenge. Parenteral routes of inoculation that achieved good protection included intramuscular and intravenous injections. Successful mucosal routes of vaccination included DNA drops administered to the nares or trachea. By far the most efficient DNA immunizations were achieved by using a gene gun to deliver DNA-coated gold beads to the epidermis. In mice, 95% protection was achieved by two immunizations with beads loaded with as little as 0.4 micrograms of DNA. The breadth of routes supporting successful DNA immunizations, coupled with the very small amounts of DNA required for gene-gun immunizations, highlight the potential of this remarkably simple technique for the development of subunit vaccines. In contrast to the DNA based antigen vaccines, the present invention provides the development of an intranasal gene transfer method using IFN-gamma, which can be used as a prophylaxis against multiple respiratory infections. In the preferred embodiment the method is used against respiratory viral infection, most preferably against RSV.

Materials and Methods

Animals

Six-week old female BALB/c mice were purchased from the Jackson laboratory (Bar Harbor, Me.) and maintained in pathogen free conditions at the animal center. All procedures were reviewed and approved by the University of South Florida and James A Haley VA Medical Center Committee on Animal Research.

Gene Construct and Gene Transfer

The mouse IFN-γ cDNA was amplified from the mouse spleen cDNA library by polymerase chain reaction (PCR) using Vent polymerase (New England Biolabs, Beverly, Mass.). The sequence of the sense and anti-sense oligonucleotide primers were as follows: sense, 5'-dTCT GGA TCC ATG AAC GCT ACA CAC TG-3' (SEQ ID NO:1); and anti-sense, 5'- dCAC CTC GAG TCA GCA GCG AC-3' (SEQ ID NO: 2), derived from Gary P. W. and Goeddle D. V. PNAS 80:5842, 1993 and IFN-gama gene Acc No. K00083 and the primers contained a BamHI and a XhoI site, respectively. Following amplification, the PCR product was eluted from the agarose gel by the freeze squeeze method (Tautz et al. 1983), purified and then digested with BamHI and XhoI. The digested product was ligated to the mammalian expression vector pcDNA3.1(+) (Invitrogen, San Diego, Calif.) at the identical sites. The resulting plasmid, referred to as pIFN-γ, was propagated in *E. coli* DH5γ cells. Large-scale plasmid DNA was prepared using a Qiagen kit (Qiagen, Chatsworth, Calif.) following the manufacturer's specifications. This produced sufficiently pure DNA with minimum endotoxin contamination. PBS, lipofectAMINE alone and pcDNA3.1 were used as controls. For intranasal gene transfer, mice were inoculated intranasaly thrice at two-day intervals, with a mixture of 100 μg of pIFN-γ DNA complexed with the cationic lipid, lipofectAMINE (Life Technologies, Gaithersburg, Md.) in a 50 μl volume.

Viral Infection of Animals and Tissue Collection

Mice were infected intranasally with RSV A2 strain (ATCC, Rockville, Md.) at a moi of 1×106 seven days after the last intranasal DNA inoculation. Animals were sacrificed on day four post-infection (p.i) and their lungs removed for RT-PCR and histopathological studies.

Epithelial Cell Culture and Virus Infection

The HEp-2 (ATCC CCL-23) cell line was obtained from the American Type Culture Collection (Rockville, Md.) and were maintained in Minimum Essential medium with Hank's salts supplemented with 5% fetal bovine serum (Atlanta Biologicals, Norcross, Ga.) at 37° C. with 5% $CO_2$. Respiratory Syncytial Virus (RSV) A2 strain was obtained from ATCC (VR-1302) and was propagated in HEp-2 cells in a monolayer culture. Viral stocks were prepared from infected HEp-2 cell after 5–6 days post infection (p.i.) and stored at −70° C. in aliquots and was used as the viral inoculum in this study.

Interferon Gamma Treatment and RSV Infection

HEp-2 cells were grown at $0.3\times10^6$ cells/ well in six well tissue culture plates, treated with IFN-γ (Atlanta Biologicals, Norcross, Ga.) at concentrations of 0,1,10,100 and 500 ng/ml, respectively, for 24 hours and subsequently infected with RSV at an moi of 33 pfu/cell. Virus was allowed to absorb for two hours at 37° C. with 5% $CO_2$. After two hours, the viral inoculum was replaced by complete medium containing the respective concentrations of IFN-γ. The cells were harvested at 24 hours, 48 hours and 72 hours post infection washed once with PSB, pH 7.4 and stored at −70° C. till ready to use.

Immunocytochemical Analysis

HEp-2 cells were treated with 100 ng/ml of IFN-γ for 24 hours and subsequently infected with RSV. Cells were harvested at 24 hours post infection, washed with PBS, pH 7.4 and suspended in the same buffer. Cell suspensions were dropped into a microscopic slide, dried, fixed in acetone and stained with FITC labeled anti-RSV mAb for 30 minutes at 37° C. in a humidified chamber. Excess stain was washed out and the slides were mounted with fluoromount G and observed under fluorescent microscope. The number of infected and uninfected cells were counted from three different slides of the same treatment group randomly from 11 different spots from each slide and the percentage of infected and uninfected cells were plotted against the time of infection.

Quantitation of RSV Titers in Lung

RSV titers in the mouse lung were quantitated by ELISA. Whole lungs were homogenized in 2 ml of lysis buffer (0.5% Triton X-100, 150 mM NaCl, 15 mM Tris, 1 mM CaCl2 and 1 mN MgCl2, pH 7.40). Homogenates were incubated on ice for 30 minutes, and then centrifuged at 3000 rpm for 10 minutes Supernatants were collected, passed through a 0.2 μm filter (Gelman Sciences, Ann Arbor, Mich.) and used for ELISA. Briefly, supernatants were first incubated in goat anti-human RSV antibody (AB1128, Chemicon, Temecula, Calif.) coated ELISA plates (Coaster, Cambridge, Mass.) and then incubated with mouse anti human RSV polyclonal antibody (NCL-RSV3, Vector Laboratories). Following incubation with peroxidase labeled goat anti mouse IgG antibody (Boehringer Manheim, Indianapolis, Ind.), immune complexes were detected using tetra methyl benzidine (TMB) as the substrate. Optical densities were read at 450 nm using an ELISA reader. The results were transformed to PFU/g lung by the standard curve obtained from known amounts of ATCC stock virus titers.

RNA Extraction Total cellular RNA was isolated from the lung tissue using TRIZOL reagent (Life Technologies, Gaithersburg, Md.) following the manufacturer's instructions. One ml of Trizol reagent was added to 50–100 mg of lung tissue and homogenized. Lung homogenate was suspended by pipeting and allowed to stand at room temperature (RT) for five min for lysis. Chloroform (200 μl) was added to each tube and mixed thoroughly. After five minutes, the cells were centrifuged at 12,000 rpm for 15 minutes at 15–200° C. The clear aqueous supernatant was transferred to a fresh tube and an equal volume of iso-propanol was added, mixed well, and centrifuged at 12,000 rpm for 15 min at 15–20° C. The RNA pellet was washed with 70% ethanol, air-dried and dissolved in diethyl-pyrocarbonate-treated water.

Reverse Transcription—Polymerase Chain Reaction (RT-PCR)

RSV replication in murine lung was monitored by checking the mRNA expression of RSV N gene. The sense and anti-sense oligonucleotide sequences were as follows: 5'-dGCG ATG TCT AGG TTA GGA AGA A-3' (SEQ ID NO: 3) and 5'-dGCT ATG TCC TTG GGT AGT AAG CCT-3' (SEQ ID NO:4). The following oligonucleotide primers were used to check the mRNA expression of mouse IFN-γ, 5'-dTCT GGA TCC ATG AAC GCT ACA CAC TG-3' (SEQ ID NO:1) and anti-sense, 5'-dCAC CTC GAG TCA GCA GCG AC-3' (SEQ ID NO:2). The primers for IL-5 were 5'-d AAG GAT GCT TCT GCA CTT GA-3' (SEQ ID NO:5) and 5'-dACA CCA AGG AAC TCT TGC A-3' (SEQ ID NO:6). The oligonucleotide primers, 5'-dGAC ATG GAG AAG ATC TGG CAC -3' (SEQ ID NO:7) and 5'-dTCC AGA CGC AGG ATG GCG TGA-3' (SEQ ID NO:8), were used to examine the expression of the mouse β-actin which was used as an internal control. For the synthesis of first strand cDNA, 1 μg of total RNA was mixed with 150ng of random primer and heated to 700° C. for 10 minutes, immediately chilled on ice for five minutes, followed by the addition of 9 μl of reverse transcription mixture prepared in a total volume of 25 μl containing 5 μl of 5X first strand buffer, 2.5 mM of each dNTP, 8 mM DTT, and 100 units of Superscript RNAse H⁻ reverse transcriptase (Life Technologies, Gaithersburg, Md.). The reaction was further incubated at 42° C. for 50 minutes. The reverse transcriptase reaction was terminated by the incubation of the reaction tubes sample at 70° C. for 10 minutes and the first strand cDNA was cooled to 4° C.

PCR amplification was carried out with a 20 μl reaction volume consisting of a PCR buffer (Life Technologies, Gaithersburg, Md.) containing 1.5 mM MgC12, 0.2 mM of each dNTP, 50 pM of each primer, and 1unit of recombinant Taq DNA polymerase (Life Technologies, Gaithersburg, Md.). The reaction mixture was denatured at 95° C. for one minute, annealed at the respective annealing temperature for one minute and extended at 72° C. for one minute. The cDNA was amplified for 25–40 cycles, followed by an extension step of seven minutes at 72° C. to extend the partially amplified products. The resultant PCR products were analyzed by electrophoresis on 1.5% agarose gel and the products visualized by staining with ethidium bromide.

Bronchial Alveolar Lavage and Cytokine Assay

Mice were sacrificed on day four p.i. by an overdose injection of pentobarbital [Nembutal (Abbott Laboratories, North Chicago, Ill.)] (0.6 g/kg) i.p. and the thorax was opened. The lung vascular bed was flushed with 2 to 3 ml of chilled saline. The trachea was exposed and canulated with a 26 G needle connected to a tuberculin syringe. The lung was then lavaged thrice with 0.5 ml of PBS and the bronchioalveolar lavage fluid (BALF) was pooled. Recovered BAL fluid volumes ranged between 75 and 85% of instilled PBS. There was no statistically significant difference in recovered BAL fluid volumes between control and experimental groups. Supernatant was collected following centrifugation of the BAL and stored at −70° C. until it was assayed for cytokines. The cell pellet was suspended in 200 μl of RPMI 1640 media supplemented with 10% FBS and a small aliquot counted using the hemocytometer. The remaining cell suspension was centrifuged onto a glass slide using a cytospin centrifuge at 1500 rpm for five minutes at room temperature. Cytocentrifuged cell smears were air dried and stained by Leukostat™ (Fisher Scientific, Atlanta, Ga.). At least 300 cells were examined in a blinded fashion for a differential cell count by microscopic observation. IFN-γ and IL-5 assay from BALF was carried out using ELISA kits from R&D systems (Minneapolis, Minn.) and Endogen (Woburn, Mass.) respectively, following the manufacturer's specifications.

Histology and Scoring for Airway Inflammation

Lungs were inflated with intratracheal injections of PBS followed by 10% neutral buffered formalin solution (Sigma Chemicals, St Louis, Mo.) to preserve the pulmonary architecture in an expanded state. Lungs were transferred to 80% ethanol after one hour and then embedded in paraffin. The sections were stained with hematoxylin and eosin.

A semi-quantitative evaluation of inflammatory cells in the lung sections, including alveolar spaces, bronchovascular bundles and interstitium, was performed. Inflammatory infiltrates were assessed morphologically for location, thickness, and cell composition. The sections were scored as follows: for epithelial damage, 0=no damage, 1=increased epithelial cell cytoplasm without desquamation, 2=epithelial desquamation without bronchial exudate composed of inflammatory cells, 3=bronchial exudate composed of desquamated epithelial cells and inflammatory cells; for interstitial cellularity, 0=no infiltrate, 1=mild, generalized increase in cellularity of the alveolar septa without thickening of the septa or significant airspace consolidation, 2=dense septal mononuclear infiltrates with thickening of septa, 3=significant alveolar consolidation in addition to interstitial inflammation; for peribronchovascular infiltrates, 0=no infiltrate, 1=infiltrate up to four cells thick in most vessels, 2=infiltrate five to seven cells thick in most vessels, 3=infiltrate greater than seven cells thick in most vessels. Data are expressed as means±standard errors.

Statistical Analysis

Histological scores were expressed as mean±standard error of mean and statistical comparisons in the two groups (controls and vaccinated) were made with Student's test. Differences between groups were considered significant at p values less than 0.05. All statistical analyses were performed with Statview II software (Abacus Concepts, Berkley, Calif.).

Results

Expression of IFN-γ in Mouse Lung Following pIFN-γ Vaccination

Mouse IFN-γ cDNA was amplified as a 486 bp BamHI-XhoI cassette, which had transcription initiation and termination codons. Ligation of this PCR product to the mammalian expression vector pcDNA3.1 put IFN-γ gene under the transcriptional control of the cytomegalovirus late gene promoter followed by the bovine poly A sequences and termination signal. The resulting plasmid pcDNA3.1-IFN-γ referred to as pIFN-γ, was transfected into NIH-3T3 cells to ascertain its expression (data not shown). The lung expression of IFN-γ was analyzed in mice following administration of the pIFN-γ. Expression of IFN-γ transcripts and the presence of the pIFN-γ constructs in the vaccinated mice were also confirmed by RT-PCR. Also, the expression of IFN-γ was examined in BALF at seven days post-treatment in mice that received either PBS, pcDNA 3.1 (mock; 100 μg/mouse), pIFN-γ or lipofectamine. As shown in FIG. 1, mice vaccinated with pIFN-γ expressed high levels of IFN-γ (62.19(14.6 pg/ml). IFN-γ levels were lower than the detection limit in all other groups of mice used as controls.

pIFN-γ DNA Vaccination Attenuates RSV Infection in a Murine Model

Figure 2A:
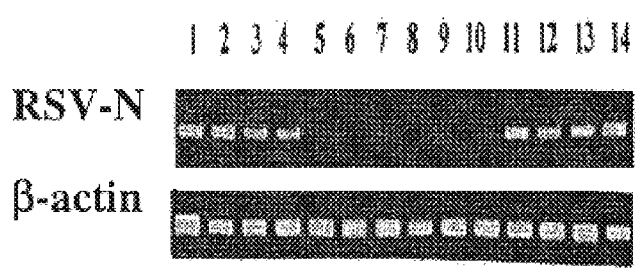
FIGS. 2A +B show detection of RSV infection in the lungs of BALB/c mice; RSV-N gene expression was checked by RT-PCR; Mice were treated with IFN-γ expressing plasmid, pIFN-γ complexed with lipofectamine (Lanes 5–10) or lipofectamine alone (Lanes 11–14) as described under methods and subsequently infected with RSV after a week of last treatment; Lanes 1–4 are controls, which were treated with PBS alone; RSV N gene expression was detected in all the control mice (lanes 1–4) and also in the mice treated with lipofectamine alone (lanes 11–14); whereas, in pIFN-γ treated mice, RSV-N gene expression was not detected (lanes 7–10) or minimally detected (lanes 5 and 6); Lower panel shows the RT-PCR of β-actin gene, used as the internal control, data are from two independent sets of experiment.
Figure 2B:
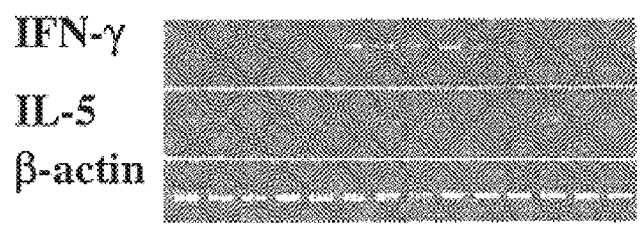
FIG. 2C shows pIFN-γ gene therapy inhibits RSV replication in mouse lung; Group of mice (n=6) were intranasaly inoculated with 100 μg of pIFN-γ complexed with lipofectamine for three times on two days interval and infected with RSV seven days later; On day four p.i. their lungs were taken out, homogenized and RSV titer was monitored by ELISA. results represent the mean±standard deviation of six mice/group.
Figure 2C:
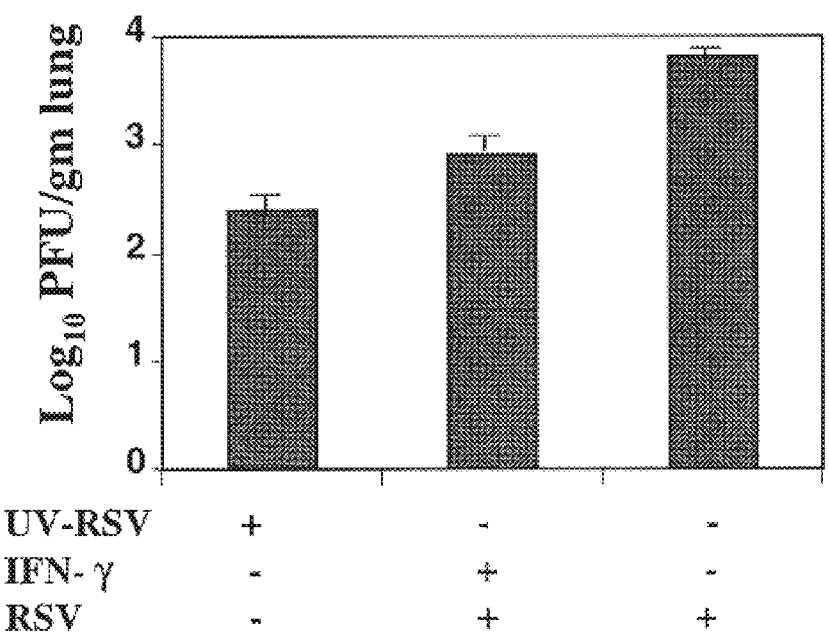
Figure 3A:
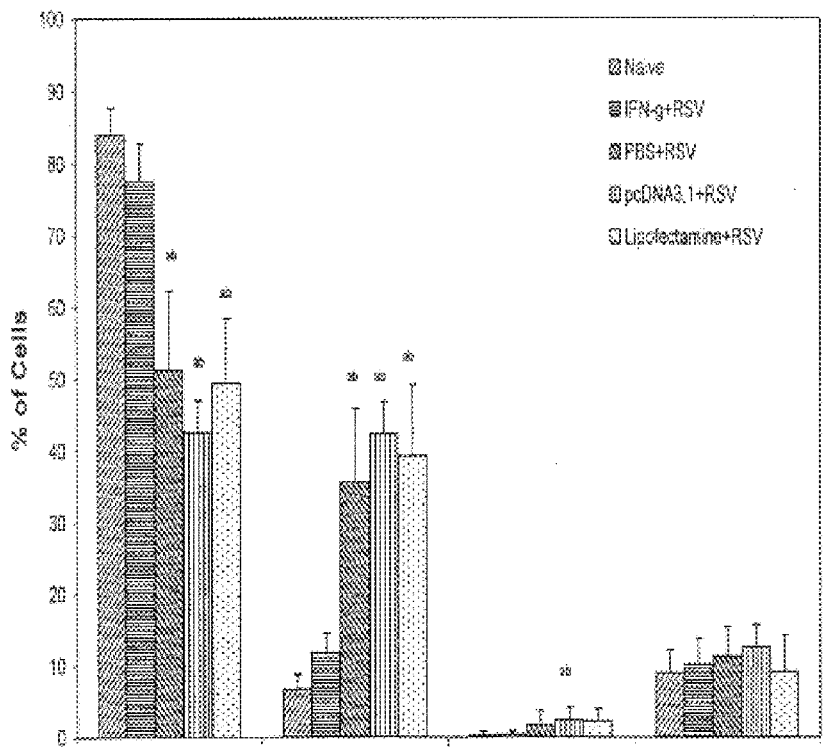
FIGS. 3 (A+B) shows an analysis of bronchial alveolar lavage; Groups of mice (n=6) were treated as described in FIG. 1 and infected with RSV seven days later; BAL was collected from the lungs of mice on day four p.i. cytocentrifuged and stained. BAL cell differential from pIFN-γ treated and control mice is shown, bars represent mean±SD. p<0.05 (n=6) compared to a: naive uninfected, b: IFN-γ vaccinated and RSV infected mice.
Figure 3B:
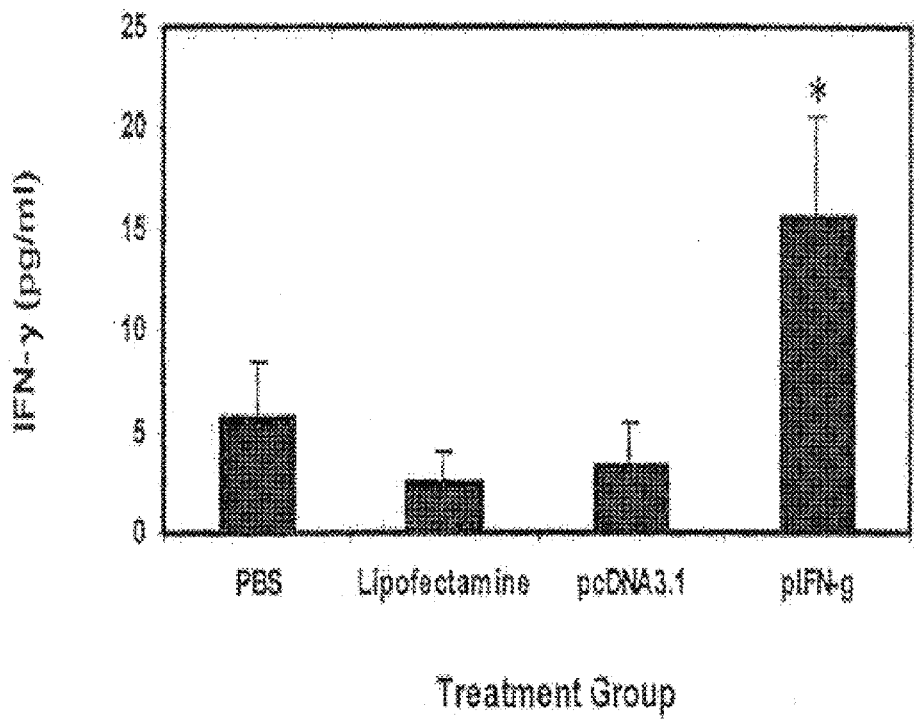

BALB/c mice, intranasaly administered with RSV, developed severe RSV infection, including lesions in their lungs by day four. RSV infection in mouse lung could be detected by RT-PCR by day two but not in mice administered with PBS or UV-inactivated RSV. To examine the effect of pIFN-γ vaccination mice were infected with 1×106 pfu of RSV, seven days after IFN-γ vaccination. RSV replication was detected in the lung tissues by RT-PCR assay of the RSV N protein (364 bp) on day four of inoculation in control mice (FIG. 2A, Panel 1, lanes 1–4 and 11–14). In marked contrast, mice vaccinated with pIFN-γ showed either none (FIG. 2A, Panel 1, lanes 7–10) or minimal RSV infection (FIG. 2A, Panel 1, lanes 5 and 6). Vaccinated mice also showed 87.01% reduction in RSV titers as observed by ELISA (FIG. 2B). These results indicate that pIFN-γ vaccination resulted in significant reduction of RSV infection in lungs of mouse inoculated with RSV.

pIFN-γ Vaccination Alters Inflammatory Cell Population in the RSV-Infected Airway and Lung The cellular composition of the airway and lung following RSV infection was examined by a BAL cell differential; the results are shown in FIG. 3. A significant (p<0.05) decrease (27.3%) in the lymphocyte count was observed in the BALF of mice treated with pIFN-γ as compared to the controls. There was also an increase in the neutrophil count following RSV infection in all groups compared to uninfected mice, however, no significant change was observed among the control groups and pIFN-γ administered mice. Eosinophil counts in all the groups were low. Naive uninfected and pIFN-γ administered and RSV infected mice showed a significant (p<0.05) reduction in eosinophil count as compared to the vector control. There was a significant reduction in macrophage cell count (p<0.05) in control groups as compared to pIFN-γ administered and naive uninfected group of mice. There was no significant change in the cell differential between mice administered with IFN-γ followed by RSV infection when compared to naive uninfected mice.

pIFN-γ Vaccination Decreases Lung Inflammation and Pathology

Figure 4:
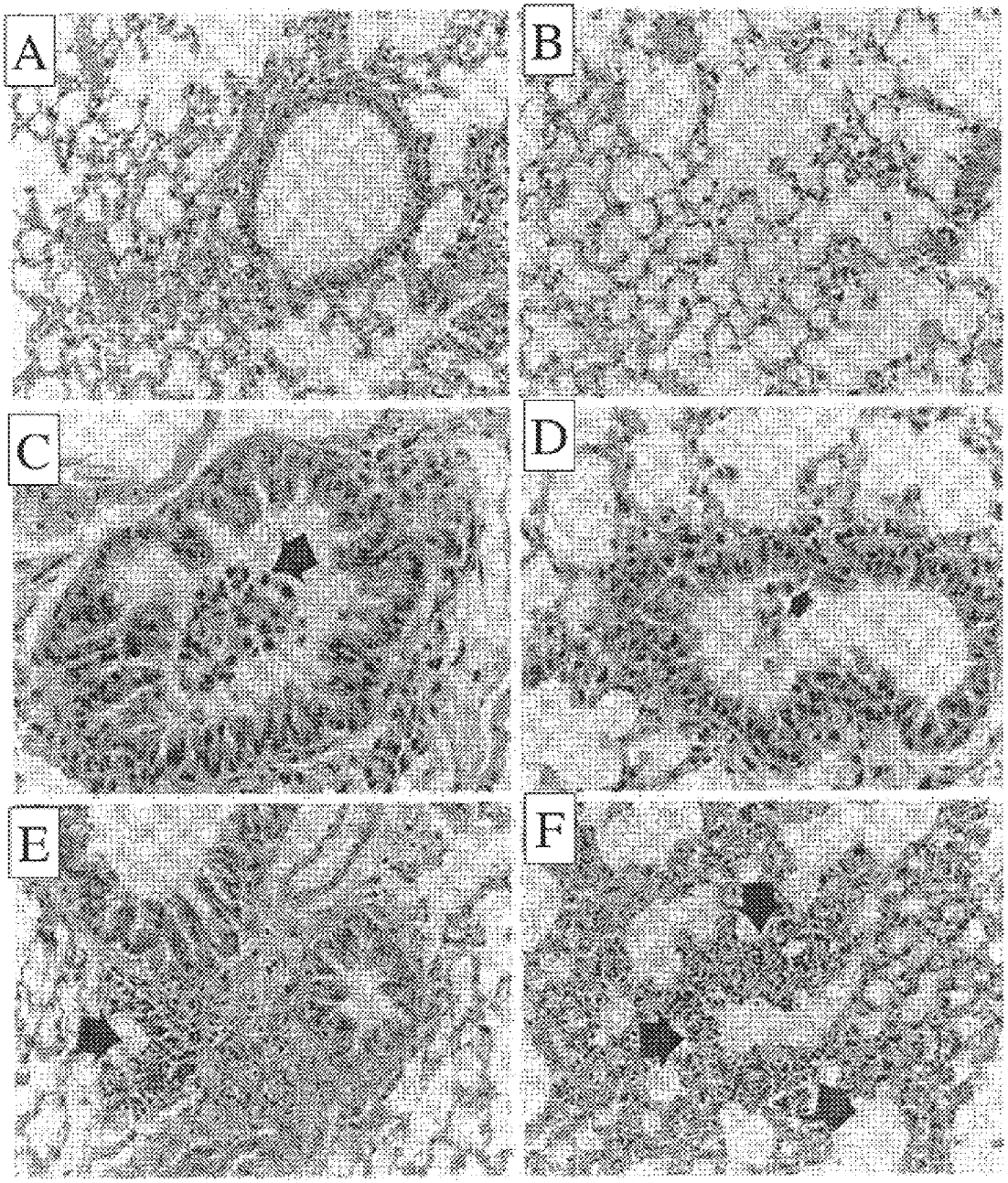
FIGS. 4 (A–F) shows an effect of pIFN-γ gene transfer on lung pathology; A and B are tissue from pIFN-γ vaccinated and RSV infected mice showing normal lung pathology; The control mice with no IFN-γ treatment showed epithelial denudation and peri-bronchial infiltration (C) and bronchial exudate composed of inflammatory cells (D). Peri-vascular infiltration (E) and enlarged septal cells with mononuclear cell infiltration (4F) were also observed in control groups.

Paraffin-embedded sections of the lungs were stained with hematoxylin-eosin (HE) and examined to determine the degree of RSV-induced inflammation (FIG. 4). The group of mice administered with pIFN-γ showed normal lung pathology (FIGS. 4A and B) similar to that of the uninfected control. Control mice infected with RSV showed various features of inflammation. The epithelial cells of affected bronchioles were swollen and occasionally, an exudate of desquamated epithelial cells was present in the lumen of some of the bronchioles (FIGS. 4C and D). Some of the alveolar spaces were densely infiltrated with mononuclear cells (FIG. 4F). Alveolar exudate and enlarged septal cells (FIG. 4F) were also present. Peri-vascular (FIG. 4E) and peri-bronchial (FIG. 4C) infiltration was observed in the control group of mice.

Semi-quantitative analysis of the lung sections based on histologic scoring for airway inflammation are summarized in Table 1. Sections were scored for epithelial damage, interstitial changes including both infiltration and thickness and peri-bronchovascular infiltration. Significant changes for all the above features were found among infected controls and IFN-γ administered and RSV infected mice.

IFN-γ Administered Down-Regulates IL-5 mRNA Expression

Figure 5:
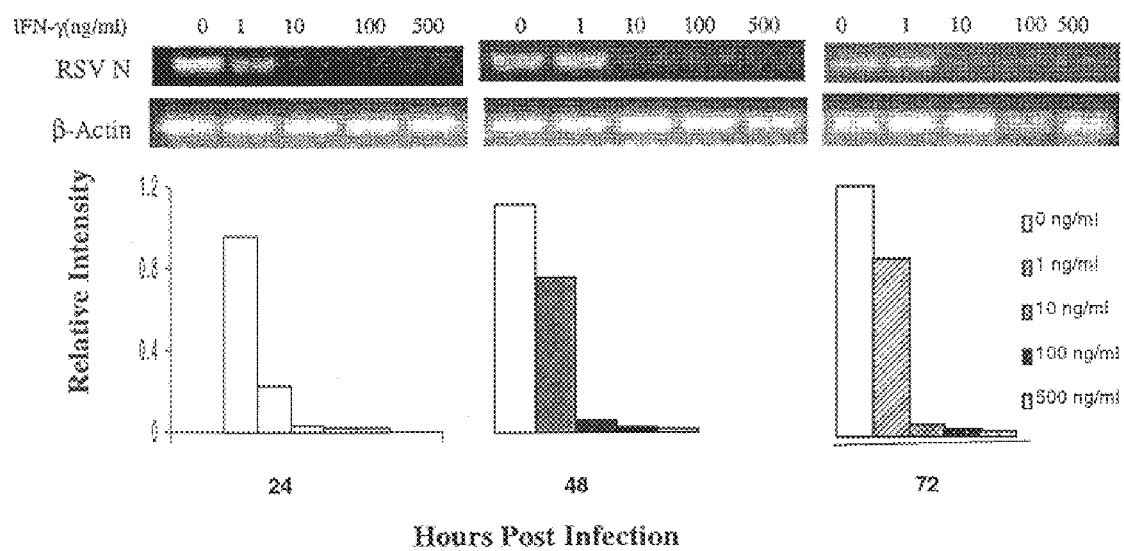
FIG. 5 (A) shows detection of IL-5 and IFN-γ mRNA expression in the lungs of BALB/c mice; Mice were treated as described in FIG. 2A and IL-5 and IFN-γ gene expression was checked by RT-PCR; Control mice (Panel 2, lanes, 1–4 and 11–14) showed IL-5 specific amplification; Vaccinated mice showed IFN-γ expression (Panel 1, lanes 6–10). Data are from two independent sets of experiment.
Figure 5:
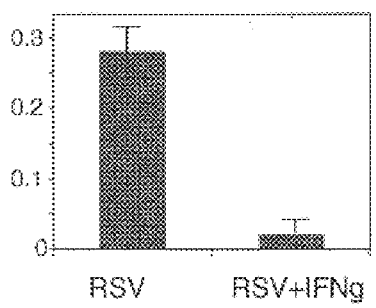
Figure 5:
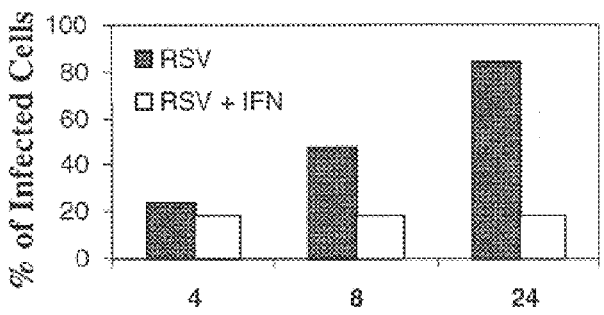

Expression of IL-5 and IFN-γ was examined by RT-PCR and ELISA in lungs of mice administered with pIFN-γ and infected with RSV seven days later. Four out of six mice administered with pIFN-γ (FIG. 5A, Panel 2, lanes 6 and 8–10) did not express mRNA for IL-5. Mice intranasaly administered with PBS or lipofectamine as controls showed IL-5 mRNA expression (FIG. 5A, Panel 2, Lanes 1–4 and 11–14). Five of six mice which were vaccinated with pIFN-γ expressed IFN-γ mRNA as detected by the RT-PCR analysis (FIG. 5A, Panel 1, Lanes 6–10). Control mice did not show any IFN-γ mRNA expression (FIG. 5A, Lanes 1–4 and 11–14). The pIFN-γ administered mouse which did not express IFN-γ MRNA also showed no reduction in IL-5 mRNA.

IFN-γ and IL-5 were also assayed by ELISA from the FALF of pIFN-gamma administered and control mice after RSV infection. All control mice showed increased IFN-γ expression after RSV infection (FIG. 5B), which was not detected earlier in an uninfected state. There was no significant difference of IFN-γ expression among the various control groups. However, the control groups expressed 2.5–6 fold higher IFN-γ expression after the RSV infection. The administered group, when compared to different controls and naive uninfected mice, showed significantly (p<0.05) higher levels of IFN-γ expression. However, we could not detect IL-5 in BALF of these groups of mice by ELISA.

IFN-γ prevents RSV replication in human bronchial apithelial cells in HEp-2 cells The mechanism underlying attenuation of RSV induced lung illness by pIFN-γ vaccination was examined in an in vitro model of RSV infection using HEp-2 cells. Viral replication within HEp-2 cells could be detected within four hours of infection by RT-PCR using primers specific for RSV-N protein gene. To examine the effect of IFN-γ on HEp-2 cells, cells were pre-incubated for 24 hours with dilutions of IFN-γ ranging from 0–500 ng/ml and infected with RSV. The results presented in FIG. 5A demonstrate that the mRNA for RSV-N gene decreased with an increase in the concentration of IFN-γ. Incubation of HEp-2 cells with IFN-γ at the concentration of 10 ng/ml and higher inhibited RSV infection of HEp-2 cells. After 24 hours of infection, RSV-N gene mRNA was not detectable. Similar results were also obtained with the RSV-ELISA (FIG. 5B). Cells treated with IFN-γ protein showed a 94% reduction in RSV titers as compared to the cells infected with RSV alone. To further investigate the effect of IFN-γ at the protein level, cells were examined by immuno-cytochemistry using FITC labeled mAb to RSV. Three slides from each group were examined at 11 different spots each in a blinded fashion and the average RSV infected and non-infected cells were plotted (FIG. 5C). The results showed that a 24 hour post infection RSV infection was 80% in untreated cells in contrast to only 13% in IFN-γ (100 ng/ml) treated cells. It was observed that the percentage of infected HEp-2 cells decreased in the IFN-γ treated cells. These results suggest that the pretreatment of cells with soluble IFN-γ can prevent RSV replication in HEp-2 cells.

Discussion

RSV infection induces a Th2-like immune response in children and may be a risk factor for asthma, a Th2 dominant disease in individuals genetically predisposed for atopic diseases. IFN-γ is a potent suppressor of Th2-like response. The systemic use of IFN-γ protein to treat respiratory tract infections or allergic disease is limited because of its short half-life. Consequently, it has to be given in high or repeated doses to reach therapeutic efficacy; however, high dose IFN-γ is cytotoxic. In an effort to circumvent the drawbacks inherent with the use of IFN-γ protein, an IFN-γ gene transfer approach was used in a murine model to inhibit allergic inflammation (Li, et al. 1996). An IFN-γ expressing plasmid vector, pIFN-γ, was used in a murine model to inhibit RSV infection and the mechanism of inhibition was studied in an epithelial cell culture system. Evidence from the studies of RSV replication, BAL and histopathology of mice indicate that IFN-γ-DNA vaccine is effective in inhibiting RSV replication and consequently infection-associated inflammation.

RSV infection induces inflammatory changes in the lung, which is readily detectable in BAL fluid. In normal or sham infected mice most recovered cells in BAL fluid are macrophages with less than 5% lymphocytes. RSV specific lymphocytes from the lungs of RSV infected mice by exhibit CTL activity, which peaks at days seven to nine, post infection (Taylor, et al. 1996). The proportion of lymphocytes increases to about 20% between 10 and 16 days after infection and decreases thereafter (Openshaw, 1989). Consistent with those findings BAL from the lungs of pIFN-γ vaccinated mice had 27% less lymphocytes compared to control groups. A small number of eosinophils were also detected in BAL of RSV infected mice, suggesting that the airway-hyper-responsiveness caused by the viral infection may be due to infiltration of these cells to the airway. RSV infection induces the expression of adhesion molecules on the bronchial epithelium, particularly ICAM-1 (Arnold, et al. 1995; Matsuzaki, et al. 1996; Arnold, et al. 1996), which contributes to airway inflammation by supporting adhesion and retention of these infiltrating inflammatory cells (Stark et al. 1996).

Viral infections induced IFN-γ, which in turn facilitates resolution of viral infection (Chonomaitre et al. 1981). Therefore, IFN-γ levels were compared in BAL fluids following infection with RSV in control and pIFN-γ vaccinated mice. Only a three to six fold increase in IFN-γ production was found in RSV infected compared uninfected mice, which is in agreement with a low level of IFN-γ induced by RSV (Chonomaitre et al. 1981). Contrary to the expected results, the pIFN-γ vaccinated and RSV infected compared to vaccinated uninfected mice showed a four-fold reduction in IFN-γ levels. The reason for this reduction is unknown. It is likely that the IFN-γ is metabolized rapidly following RSV infection.

IFNs also possess important immunomodulatory functions. Because of the reciprocal regulated of T helper cell subsets it was anticipated that the pIFN-γ vaccine would promote the Th1-like instead of a Th2-like immune response expected against RSV. The cytokine IL-5 is an important marker of Th2-like immunity induced by RSV and it plays a pivotal role in eosinophil survival in the lung and asthma. Results from RT-PCR analysis of IL-5 MRNA expression indicated that pIFN-γ vaccination resulted in expression of IFN-γ mRNA expression and inhibited IL-5 expression in infected mice when compared to controls. Mice lacking IFN-γ mRNA expression exhibited an upregulation in the levels of IL-5 mRNA. Furthermore, IL-5 protein could not be detected in the BAL fluid of infected mice, which expressed significant amounts of IFN-γ and had only a few eosinophils. Results from RT-PCR analysis of IL-12 also showed an increased expression of IL-12 mRNA in pIFN-γ vaccinated mice. Together, these results suggest that pIFN-γ vaccine inhibits induction of IL-5 mRNA and may play an important role in the induction of a Th2-like immunity against RSV.

Epithelial cell damage and cellular infiltration are hallmarks of the RSV infection in humans and in various animal models. Prior vaccination of mice with the pIFN-γ significantly reduced epithelial cell damage and decreased interstitial and peribronchovascular infiltration of the cells in the lung upon RSV infection. The control RSV-infected mice perdominantly showed a mononuclear cell infiltrate with very few eosinophils. No marked difference was observed between the uninfected naive and pIFN-γ vaccinated and RSV infected mice, suggesting that pIFN-γ vaccination does not alter the inflammatory cell population in the lung. These findings show that the pIFN-γ per se does not induce any inflammatory changes in the airway and the mice does not exhibit any external signs of illness, which show that the vaccine is safe in mice. The evidence that pIFN-γ vaccinated and RSV infected mice exhibited a normal airway phenotype show that indeed the RSV replication is inhibited almost completely.

To study the mechanisms by which pIFN-γ induces protection against the RSV infection the effect of IFN-γ in an epithelial cell line HEp-2 as RSV infection causes epithelial cell damage leading to inflammation was studied. Pretreatment of epithelial cells with as low as 10 ng/ml of IFN-γ protein could inhibit RSV replication at 24 hours as demonstrated by RT-PCR and RSV ELISA. Cells, which were not treated, showed RSV infection. A 94% reduction in RSV titer was observed in cells treated with 100 ng/ml of IFN-γ as demonstrated by the ELISA. Immunocytochemical studies demonstrate that number of RSV infected cells increases with time and at 24 hours p.i. 80% of the cells are infected with RSV whereas, 13% of cells only were RSV positive which were treated with IFN-γ.

In summary, these results taken together demonstrate that a pIFN-γ DNA vaccination inhibits RSV replication, alters the lung cytokine pattern from a Th2-dominate to Th1-dominate milieu, and protects lung from RSV-induced epithelial damage and cellular infiltration. The vaccination renders significant protection of BALB/c mice against RSV infection. The antiviral effect of IFN-γ is mediated through the activation of the 2'–5' AS system. Because of the anti-viral property of IFN-γ, an IFN-γ DNA vaccine may be useful against respiratory viral infections.

Example 2

A plasmid expressing IFN-γ gene referred to as pIFN-γ was developed to investigate its effects in reducing RSV-associated lung disease in BALB/c mice.

Intranasal administration of the pIFN-γ results in the expression of IFN-γ protein (62.19±14.6 pg/ml) and decreased RSV replication in the lung. RT-PCR results demonstrate that vaccinated mice exhibit more than a 90% reduction in RSV infection as compared to the different controls. The mice vaccinated with pIFN-γ versus controls and then infected with RSV exhibited a 27.3% decrease ($p<0.05$) in the bronchoalveolar lavage lymphocyte count. Control mice also exhibit an increase neotrophil count as compared to vaccinated mice. Few eosinophils are present following RSV infection in both controls and pIFN-γ vaccinated mice. A significant reduction in epithelial cell damage, infiltration of mononuclear cells in the peribron chiolar and perivascular regions and thickening of the septa occur in the lungs of mice vaccinated with pIFN-γ compared to controls.

Semi-quantitative Scoring of the Histopathology

| Treatment Group | Epithelial Damage | Interstitial Change | Peri-broncho-vascular change |
|---|---|---|---|
| Control + RSV | 2.0 ± 0.2 | 1.4 ± 0.2 | 1.9 ± 0.2 |
| Vaccinated + RSV | 1.1 ± 0.2* | 0.3 ± 0.2** | 0.9 ± 0.1** |
| Naïve | 0.8 ± 0.2* | 0.33 ± 0.3 | 0.8 ± 0.1 | n = 12;
*value significant at $p < 0.05$,
**value significant at $p < 0.01$

These data shows that pIFN-γ vaccination decreases RSV replication and pulmonary inflammation. pIFN-γ can be useful to present RSV infection.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Adams, R. B., Planchon S. M., Roche J. K. IFN-gamma modulation of epithelial barrier function time course, revesibility, and site of cytokine binding. J. Immunol. 1993; 150-2356-63.

Armstrong, D. S. and Menahem S. Cardiac arrythmias as a manifestation of acquired heart disease in association with pediatric respiratory syncytial virus infection. J. Ped. Child Health. 1993; 29:309–311.

Arnold R, Werchau H, Konig W. Expression of adhesion molecules (ICAM-1, LFA-3) on human epithelial cells (A549) after respiratory syncytial virus infection. Int Arch Allergy And Immunol. 1995;107:392–93.

Arnold R, Konig W. ICAM-1 expression and low-molecular-weight G-protein activation of human bronchial epithelial cells (A549) infected with RSV. J Leuk Biol 1996;60:766–71.

Ausubel et al., Current Protocols in Molecular Biology, John Wiley and Sons, Baltimore, Md. (1989)

Barik S. Transcription of human respiratory syncytial virus genome RNA in vitro: requirement of cellular factor(s). J. Virol. 1992; 66:6813–6818.

Becker S et al. Interleukin-8 Expression in Normal Nasal Epithelium and its Modulation by Infection with Respiratory Syncytial Virus and Cytokines Tumor Necrosis Factor, Interleukin-1 and Interleukin-6. AM J. Respir. Cell Mol. Biol. 1993. 8:20–7.

Beretta, L., M. Gabbay, R. Berger, S. M. Hanash, and N. Sonenberg. Expression of the protein kinase PKR is modulated by IRF-1 and is reduced is 5q-associated leukemias. Oncogene. 1996; 12:1593–1596.

Birren et al (eds) Genome Analysis: A Laboratory Manual Series, Vols. 1–4 Cold Spring Harbor Laboratory Press, New York (1998)

Blood 87:3822

Boehm U., Klamp T., Groot, M., Howard J. C. Cellular responses to interferon-gamma. Annu Rev immunol. 1997;15:749–95.

Brandt C D, Kim H W, Arrobio J O et al. Epidemiology of respiratory syncytial virus infection in Washington, D.C. III. Composite analysis of eleven consecutive yearly epidemics. Am J Epidemiol 1990; 98:355–64.

Center for Disease Control and Prevention: Respiratory syncytial virus activity: United States. 1996–1997 season, MMWR 1996;45:1053.

Chanock, R. M., H. W. Kim, C. Brandt, and R. H. Parrott. Respiratory syncytial virus. In Viral infections of humans. A. S. Evans, editor. Plenum Publishing Corp., New York. 1976; 365–382.

Chanock R M, Parott R H. Acute respiratory disease in infancy and childhood: present understanding and prospects for prevention. Pediatrics 1981;36:21–39.

Chanock R M, Parrott R H, Connors M, Collins P L, Murphy B R. Serious respiratory tract disease caused by respiratory syncytial virus: prospects for improved therapy and immunization. Pediatrics 1992;90:137–43.

Choi, A M, Jacoby D B. Influenza Virus A Infection Induces Interleukin-8 Gene Expression in Human Airway Epithelial Cells. FEBS Lett. 1992; 309:327–9.

Churchill, L., F. H. Chilton, J. H. Resau, R. Bascom, W. C. Hubbard, and D. Proud. Cyclooxygenase metabolism of endogenous arachidonic acid by cultured human tracheal epithelial cells. Am. Rev. Respir. Dis. 1989; 140:449.

Churchill, L., B. Friedman, R. P. Schleimer, and D. Proud. Production of pranuloyte-macrophage colony stimulating factor by cultured human tracheal epithelial cells. Immunology. 1992; 75:189.

Chonomaitre T, Roberts N J Jr, Douglas R G Jr., Hall C B, Simons R L. Interferon production by human mononuclear leukocytes: differences between respiratory syncytial virus and influenza virus. Infect Immun 1981;32:300–03.

Clemmens, M. J., and B. R. G. Williams. Inhibition of cell-free protein synthesis by pppA2'p5'A2'p5'A: a novel oligonucleotide synthesized by interferon-treated L cell extracts. Cell 1978; 13:565–572.

Coccia, E. M., G. Marziali, E. Stellaci, E. Perrotti, R. Ilari, R. Orsatti, and A. Battistinni. Cells resistance to interferon-β respond to interferon-γ via the Stat1-IRF-1 pathways. Virology. 1995; 211:113:122.

Cohen, B., D. Peretz, D. Vaiman, P. Benech, and J. Chebath. Enhancer-like intereferon responsive sequence of the human and murine (2'-5') oligoadenylate synthetase gene promoters. EMBO. J. '988; 7:1411–1419.

Colgan, S P, Parkos C A, Matthews J B et al. IFN gamma induces a cell surface phenotype switch on T84 intestinal epithelial cells. Am J Physiol 1994; 1267:C402–10.

Collins, P L. The molecular biology of human respiratory syncytial virus (RSV) of the genus Pneumovirus. In: The Paramyxoviruses (ed. Kingsbury, D W), Plenum, New York, 1991; 103–162.

Collins et al., 1996

Connors M, Kulkarni A B, Firestone C Y, Holmes K L, Morse III H C, Sotnikov A V, Murphy B R. Pulmonary histopathology induced by respiratory syncytial virus (RSV) challenge of formalin-inactivated RSV-immunized BALB/c mice is abrogated by depletion of CD4+T cells. J Virol 1992;66:7444–51.

Connors M, Geise N A, Kulkarni A B, Firestone C Y, Morse III H C, Sotnikov A V, Murphy B R. Enhanced pulmonary histopathology induced by respiratory syncytial virus (RSV) challenge of formalin-inactivated RSV-immunized BALB/c mice is abrogated by depletion of interleukin-4 (IL-4) and IL-10. J Virol 1994;68:5321–25.

Cregg J M, Vedvick T S, Raschke W C: Recent Advances in the Expression of Foreign Genes in Pichia pastoris, Bio/Technology 11:905–910, 1993

Cromwell, O., Q. Hamid, C J Corigan, J Barkans Q Meng P D Collins, and A B Kay. Expression and generation of interlukin-8, IL-6 and granulocytemacrophage colony stimulating factor by bronchial epithelial cells and enhancement of IL-1β and tumor necrosis factor-α. Immunology. 1992; 77:5834.

Crowe J E Jr Vaccine 1998 Aug–Sep; 16(14–15):1423–32 Immune responses of infants to infection with respiratory viruses and live attenuated respiratory virus candidate vaccines.

Culver, 1998. Site-Directed recombination for repair of mutations in the human ADA gene. (Abstract) Antisense DNA & RNA based therapeutics, February, 1998, Coronado, Calif.

Dao, T, Takeuchi M, Fukuda S et al. Natural human IFN alpha enhances the expression of ICAM-1, integrin alpha 2 and beta 1 by a mucosal eopithelial cell line. Folia Biologica. 1995; 41:213–25.

Darnell, J. E. Jr., I. M. Kerr, and G. R. Stark. Jak-STAT pathways and transcriptional activation in response to IFNs and other extracellular signalling proteins. Science. 1994; 264:1415–1421.

Darnell Jr. J E. STATs and Gene regulation. Science. 1997; 277:1630163.

Diaz-Guerra, M., C. Rivas, and M. Esteban. Inducible expression of the 2-5A synthetase/RNase-L system results in inhibition of vaccinia virus replication. Virology. 1997; 227:220–228.

Farrar, M. A., and R. D. Schreiber. The molecular cell biology of IFN-γ and its receptor. Ann. Rev. Immunol. 1993; 11:571–611.

Fixler D E. Respiratory syncytial virus infection in children with congenital heart disease. Ped Cardiol 1996; 17:163–8.

Floyd-Smith, G., E. Slattery, and P. Lengyel. Interferon action: RNA cleavage pattern of a (2'-5') oligoadenylate-dependent endonuclease. Science. 1981; 212:1020–1032.

Fujita, T., L. F. Reis, N. Wantabe, Y. Kimura, T. Taniguchi, and J. Vlcek. Induction of the transcription factor IRF-1 and interferon-β mRNAs by cytokines and activators of second messenger pathways. Proc. Natl. Acad. Sci. USA. 1989; 89:9936–9940.

Garofalo R. Mei F. Espejo R. Ye G. Haeberle H. Baron S. Orga P L. Reyes V E. Respiratory syncytial virus infection of human respiratory epithelial cells up=regulates class I MHC expression through the induction of IFN-beta nd IL-1 alpha. J Immunol. 1996; 157(6):2506–13.

Gilboa, E, Eglitis, M A, Kantoff, P W, Anderson, W F: Transfer and expression of cloned genes using retroviral vectors. BioTechniques 4(6):504–512, 1986.

Graham B S, Henderson G S, Tang Y W, Lu X, Neuzil K M, Colley D G. Priming immunization determines T helper cytokine mRNA expression patterns in lungs of mice challenged with respiratory syncytial virus. J Immunol 1993; 151:2032–40.

Hall C B, Walsh E E, Long C E, Schnabel K C. Immunity to and frequency of reinfection with respiratory syncytial virus. J Infect Dis 1991;163:693–98.

Hall C B, McBride J T. Respiratory syncytial virus-from chimps with colds to conundrums and cures. New Engl J Med 1991;325:57–8.

Hall C B. Prospects for a respiratory syncytial virus vaccine. Science 1994;265:1393–94.

Hall et al. 1984

Harada H. Matsumoto M. Sato M. et al. Regulation of IFN-alpha/beta genes: evidence for a dual function of the transcription factor complex ISGF3 int he production and action of IFN-alpha/beta. Genes to Cells. 1996. 1(11):995–1005.

Holtzman M J, B. Fredman, A. Bohrer, and J. Turk. Synthesis of the 1-0-hexadecyl molecular species of platelet-activating factor by airway epithelial and vascular endothelial cells. Biochem. Biophys. Res. Commun. 1991. 177:357

Holtzman M J, Brody S L, Look D C. Does gene therapy call for STAT immunity and inflammation at the epithelial barrier. Am J Respir Cell Mol Biol. 1995. 12:127–129.

Hovanessian, A. G., R. E. Brown, and I. M. Kerr. Synthesis of low molecular weight inhibitor of protein synthesis with enzyme from interferon-treated cells. Nature. 1977; 268:537–539.

Ihle, J. N. 1996. STATs: signal transducers and activators of transcription. Cell. 1996; 84:331–334.

Improta, et al. 1997

Jin FY. Natan C. Radzioch D. Ding A. Secretory leukocyte protease inhibitor: a macrophage product induced by and antagonistic to bacterial lipopolysacharide. Cell. 1997. 88(3):417–26.

Karupiah, G., Q. W. Xie, R. M. Buller, C. Nathan, C. Duarte, J.D. MacMicking. Inhibition of viral replication by interferon gamma induced nitric oxide synthase. Science. 1993; 261:1445–1448.

Kerr, I. M., and R. E. Brown. PppA2'p5'A2'p5'A: an inhibitor of proten synthesis synthesized with an enzyme fraction from interferon-treated cells. Proc. Natl. Acad. Sci. USA. 1978; 75:256–260.

Korutla L. Kumar R. Mechanism of interferon action: in vivo activation of 91 kDa transcription factor. Anticancer Research. 1996. 16(5A):2789–95.

Kim H W, Arrobio J O, Brandt C D et al. Epidemiology of respiratory syncytial virus infection in Washington, D.C. I. Importance of the virus in different respiratory tract disease syndromes and temporal distribution of infection. Am J Epidemiol 1973;98:216–25.

Kirshnan K. Pine R., Krolewski J J. Kinase-deficient forms of Jakl and Tyk2 inhibit interferon alpha signaling in a dominant manner. Eur J Biochem 1997. 247(1):298–305.

Kwon, O J, B T Au, P D Collins, J N Baraniuk, I M Adcock, K F Chung, and P J Barnes. Inhibitation of interlukin-8 expression by dexamethasone in human cultured airway epithelial cells. Immunology. 1994. 81:389.

Lemen, 1995

Li XM, Chopra R K, Chou T Y, Schofield B H, Wills-Karp M, Huang S K J Immunol 1996 Oct. 15;157(8):3216–9 Mucosal IFN-gamma gene transfer inhibits pulmonary allergic responses in mice.

Li X M, Chopra R K, Chou T Y, Schofield B H, Wills-Karp M, Huang S K. Mucosal IFN-? gene transfer inhibits pulmonary allergic responses in mice. J Immunol 1996;157:3216–19.

Marini, et al. 1992

Matsuzaki Z, Okamoto Y, Sarashina N, Ito E, Togawa K, Saito I. Induction of intercellular adhesion molecule-1 in human nasal epithelial cells during respiratory syncytial virus infection. Immunology 1996;88:565–68.

Merolla, et al. 1995

McIntosh K, Chanock R M. Respiratory syncytial virus. In: Fields B N, Knipe D M. (Eds.), Virology, 2nd ed. Raven Press, New York, 1990, pp.1045–1072.

Mok J Y K, Simpson H. Symptoms, atopy and bronchial reactivity after lower respiratory infection in children. Arch Dis Child 1984;59:299–305.

Mosmann T R, Coffinan R I. Th1 and Th2 cells: different patterns of lymphokine secretion lead to different functional properties. Annu Rev Immunol 1989;7:145–73.

Muller U, Steinhoff U, Reis L F L, Hemmi S, Pavlovic J, Zinkernagel R M, Aguet M. Functional role of type I and type II interferons in antiviral defense. Science 1994;264:1918–21.

Murray A R, Dowell S F. Respiratory syncytial virus: not just for kids. Hospital Practice 1997;15:87–104.

Murray et al., 1997

Naik, et al. 1997

Nilsen, T. W., P. A. Maroney, and C. Baglioni. Synthesis of (2',5') oligoadenylate and activation of an endoribonuclease in interferon-treated HeLa cells infected with reovirus. J. Virol. 1982; 42:1039–1045.

Noah, T L, Becker S. Respiratory Syncytial Virus-induced Cytokine Production by a Human Bronchial Epithelial Cell Line. Am. J. Physiol. 1993; 265:L472–8.

Openshaw PJM. Flow cytometric analysis of pulmonary lymphocytes from mice infected with respiratory syncytial virus. Clin Exp Immunol 1989;75:324–28.

P C R Protocols: A Guide To Methods And Applications, Academic Press, San Diego, Calif. (1990)

Pene J, Rousset F, Briere F, Chretien I, Bonnefoy J Y, Spits H, Yokota T, Arai N, Arai K I, Banchereay J, Vries J de. IgE production by human lymphocytes is induced by interleukin-4 and suppressed by interferons gamma, alpha and prostaglandin E2. Proc Natl Acad Sci U.S.A 1988;85:6880–84.

Perbal, A Practical Guide to Molecular Cloning, John Wiley & Sons, New York (1988), and in Watson et al., Recombinant DNA, Scientific American Books, New York Persson, C G A, Erjefalt J S Anderson M et al. Epithelium, microcirculation, and eosinophils-new aspects of the allergic airway in vivo. Allergy. 1997. 52:241–255.

Pine, R. Constitutive expression of an ISGF2/IRF1 transgene leads to interferon independent activation of interferon-inducible genes and resistance to virus infection. J. Virol. 1992; 66:4470–4478.

Pottratz T. Weir Al. Gamma-interferon inhibits pneumocystis carinii attachment to lung cells by decreasing expression of lung cell-surface integrins. Eur J Clin Invest. 1997 27(1): 17–22.

Pullen et al. 1982

Robinson et al. 1997

Roman M, Calhoun W J, Hinton K L, Avendano L F, Simon V, Escobar A M, Gaggero A, Diaz P V. Respiratory syncytial virus infection in infants is associated with predominant Th-2-like response. Am J Resp Crit Care Med 1997;156:190–95.

Sabauste, M C et al. Infection of a human erspiratory epithelial cell line with rhinovirus. Induction of cytokine release and modulation of susceptibility to infection by cytokine exposure. J. Clin Invest, 1995 96:549.

Sambrook et al., Molecular Cloning: A Laboratory Manual, Cold Spring Harbor Laboratory Press, New York (1989)

Schindler, C., J. E. Darnell Jr. Transcriptional responses to polypeptide ligands: the JAK-STAT pathways. Annu, Rev. Biochem. 1995; 64:621–651.

Schwarze J, Hamelmann E, Bradley K L, Takeda K, Gelfand E W. Respiratory syncytial virus infection results in airway hyperresponsiveness and enhanced airway sensitization to allergen. J Clin Invest 1997;100:226–233.

Sethi S K, Bianco A, Allen J T, Knight R A, Spiteri M A. Interferon-gamma down-regulates the rhinovirus-induced expression of intercellular adhesion molecule-1 (ICAM-1) on human airway epithelial cells. Clin Exp Immunol 1997;1 10:362–369.

Sethi S K, Bianco A, Allen J T, Knight R A, Spiteri M A Clin Exp Immunol 1997 Dec;110(3): 362–9 Interferon-gamma (IFN-gamma) down-regulates the rhinovirus-induced expression of intercellular adhesion molecule-1 (ICAM-1) on human airway epithelial cells Shelhamer J H et al. NIH Conference. Airway Inflammation. Ann Int Med. 1995. 123:288–304.

Silverman, R. H. 2-5A dependent RNase L: a regulated enddoribonuclease in the interferon system. In G. D'Alessio, 2nd, and J. F. Riordan (ed.), Ribunuclease: structure and function. Academic Press, New York, N.Y. 1997: 515–551.

Sly P D, Hibbert M E. Childhood asthma following hospitalization with acute viral bronchiolitis in infancy. Pediatr Pulmonol 1989;7:153–58.

Sousa, et al. 1994

Stark, G. R., W. J. Dower, R. T. Schimke, R. E. Brown, and I. M. Kerr. 2-5A synthetase: assay, distribution and variation with growth or hormone status. Nature. 1979; 278:471–473.

Stark J M, Godding V, Sedgwick J B, Busse W W. Respiratory syncytial virus infection enhances neutrophil and eosinophil adhesion to cultured respiratory epithelial cells. Roles of CD18 and intercellular adhesion molecule-1. J Immunol 1996;156:4774–82.

Tautz D, Renz M. An optimized freeze-squeeze method for the recovery of DNA fragments from agarose gels. Anal Biochem 1983;132:14–19.

Taylor G, Stott E J, Hayle A J. Cytotoxic lymphocytes from the lung of mice infected with respiratory syncytial virus. J Gen Virol 1985;66:2533–38.

Testoni et al, 1996

Valente, G., L. Ozmen, F. Novelli, M. Geuna, G. Palestro, G. Forni, and G. Garotta. Distribution of IFN-γ receptor in human tissues. Eur. J. Immunol. 1992; 22:2403–2412.

Walsh J A. Establishing Health Priorities in the Developing World. United Nations Development Programme, New York, 1988.

Warren K S. New scientific opportunities and old obstacles in vaccine development. Proc Natl Acad Sci USA 1986;83:9275–7.

Weiss S T, Tager I B, Munoz A, Speizer F E. The relationship of respiratory infection in early childhood to the occurrence of increased levels of bronchial responsiveness and atopy. Am Rev Res Dis 1985;131:573–78.

Will A, Hemmann U, Horn F, Rollinghoff M, Gessner A. Intracellular murine IFN-? mediates virus resistance, expression of oligoadenylate synthetase, and activation of STAT transcription factors. J Immunol 1996;157:4576–83.

Williams, B. R. G., R. R. Golgher, R. E. Brown. C. S. Gilbert and I. M. Kerr. Natural occurrence of 2-5A in interferon-treated EMC virus-infected L cells. Nature. 1979; 282:582–586.

Wreschner, D. H., J. W. McCauley, J. J. Skehel, and I. M. Kerr. Interferon action: sequence specificity of the ppp(A2'p)nA-dependent ribonuclease. Nature. 1981; 289:414–417.

Wyde P R Antiviral Res 1998 Aug;39(2):63–79 Respiratory syncytial virus (RSV) disease and prospects for its control

---

What is claimed is:

1. A method of inhibiting an RSV infection by intranasally administering a plasmid DNA which encodes IFN-gamma operatively linked to a viral promoter.

2. The method according to claim 1, wherein the intranasal administration includes administrating the DNA by intranasal inhalation.

3. A method to treat a mammal to inhibit an RSV infection, the method comprising intranasally administering to the mammal a therapeutic composition comprising:
   (a) a recombinant construct comprising a plasmid DNA encoding IFN-gamma operatively linked to a viral promoter;
   (b) wherein IFN gamma is expressed at or adjacent to repiratory epithelial cells; and
   (c) wherein expression of IFN-gamma results in reduced proliferation of the RSV infection.

4. A method of inhibiting an RSV infection in a host, which comprises intranasally administering to the host an effective amount of a plasmid vector comprising a first plasmid DNA sequence encoding an IFN-gamma protein, and a viral promoter sequence operatively coupled to the first plasmid DNA sequence.

5. A process for inducing a inhibitory response against RSV infection in a mammal comprising:
   intranasally administering into the respiratory tract of the mammal a construct comprising a noninfectious, nonintegrating plasmid DNA sequence encoding an IFN-gamma linked to a promoter sequence which can control the expression of the DNA sequence in the mammal, in an amount sufficient that uptake of the construct occurs, and sufficient expression results to increase levels of the IFN-gamma in the respiratory tract to provide the protective response.

* * * * *

SEQUENCE LISTING

```
<160> NUMBER OF SEQ ID NOS:  8

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 1
tctggatcca tgaacgctac acactg                                           26

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 2
cacctcgagt cagcagcgac                                                  20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 3
gcgatgtcta ggttaggaag aa                                               22

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 4
gctatgtcct tgggtagtaa gcct                                             24

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5
aaggatgctt ctgcacttga                                                  20

<210> SEQ ID NO 6
<211> LENGTH: 18
<212> TYPE: DNA
<213> ORGANISM: Artificial Sequence
<220> FEATURE:
```

```
<223> OTHER INFORMATION: Description of Artificial Sequence: primer

<400> SEQUENCE: 6
acaccaagga actcttgc                                                 18

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 7
gacatggaga agatctggca c                                             21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 8
tccagacgca ggatggcgtg a                                             21
```